US007339090B2

(12) United States Patent
Christmann

(10) Patent No.: US 7,339,090 B2
(45) Date of Patent: Mar. 4, 2008

(54) MICROINJECTION DEVICES AND METHODS OF USE

(75) Inventor: Leandro Christmann, Watkinsville, GA (US)

(73) Assignee: AviGenics, Inc., Athens, GA (US)

( * ) Notice: Subject to any disclaimer, the term of this patent is extended or adjusted under 35 U.S.C. 154(b) by 13 days.

(21) Appl. No.: 11/159,973

(22) Filed: Jun. 23, 2005

(65) Prior Publication Data
US 2005/0246783 A1 Nov. 3, 2005

Related U.S. Application Data

(63) Continuation-in-part of application No. 09/919,143, filed on Jul. 31, 2001, now abandoned.

(60) Provisional application No. 60/652,324, filed on Feb. 11, 2005, provisional application No. 60/269,012, filed on Feb. 13, 2001.

(51) Int. Cl.
*A01K 67/027* (2006.01)
*C12N 15/00* (2006.01)
*A61M 1/00* (2006.01)
*A61M 5/00* (2006.01)

(52) U.S. Cl. .......................... 800/19; 800/21; 604/27; 604/181

(58) Field of Classification Search ............... 800/19, 800/21; 604/27, 181
See application file for complete search history.

(56) References Cited

U.S. PATENT DOCUMENTS

| | | | |
|---|---|---|---|
| 4,907,158 A | 3/1990 | Kettler et al. | |
| 4,997,763 A | 3/1991 | Hughes et al. | |
| 5,011,780 A | 4/1991 | Perry | |
| 5,162,215 A | 11/1992 | Bosselman et al. | |
| 5,175,384 A | 12/1992 | Krimpenfort et al. | |
| 5,225,750 A | 7/1993 | Higuchi et al. | |
| 5,340,740 A | 8/1994 | Petitte et al. | |
| 5,434,340 A | 7/1995 | Krimpenfort et al. | |
| 5,591,669 A | 1/1997 | Krimpenfort et al. | |
| 5,656,479 A | 8/1997 | Petitte et al. | |
| 5,784,992 A | 7/1998 | Petitte et al. | |
| 6,027,722 A | 2/2000 | Hodgson | |
| 6,143,564 A | 11/2000 | Wakayama et al. | |
| 6,331,659 B1 | 12/2001 | Wakayama et al. | |
| 6,376,743 B1 | 4/2002 | Yanagimachi | |
| 2002/0028488 A1* | 3/2002 | Singh et al. | 435/70.21 |
| 2003/0126629 A1* | 7/2003 | Rapp et al. | 800/19 |
| 2004/0210954 A1* | 10/2004 | Harvey et al. | 800/19 |
| 2005/0198700 A1* | 9/2005 | Christmann et al. | 800/19 |
| 2005/0273873 A1* | 12/2005 | Christmann et al. | 800/19 |
| 2006/0123504 A1* | 6/2006 | Leavitt et al. | 800/19 |
| 2006/0174364 A1* | 8/2006 | Christmann et al. | 800/19 |

FOREIGN PATENT DOCUMENTS

| | | |
|---|---|---|
| WO | WO 90/11355 | 3/1989 |
| WO | WO 97/47739 | 6/1996 |
| WO | WO 99/10505 | 8/1997 |
| WO | WO 99/19472 | 10/1997 |
| WO | WO 99/37143 | 1/1998 |
| WO | WO 99/42569 | 2/1998 |
| WO | WO 99/47642 | 3/1998 |
| WO | WO 00/09674 | 8/1998 |

OTHER PUBLICATIONS

Perry, Mammalian Transgenesis by Intracytoplasmic Sperm Injection. *Science*, 1999; 284:1180-1183.
Naito, et al, Introduction of Exogenous DNA Into Somatic and Germ Cells of Chickens by Microinjection into the Germinal Disc of Fertilized Ova. *Mol. Reprod. Development*, 1994; 37:167-171.
Bachiller, et al., Liposome-Mediated DNA Uptake by Sperm Cells. *Mol. Reprod. Dev.*, 1991; 30:194-200.
Nakanishi and Iritani, Gene Transfer In The Chicken by Sperm-Mediated Methods. *Mol. Reprod. Dev.*, 1993; 36:258-261.
Rudolf Jaenisch, Retroviruses and Embryogenesis: Microinjection of Moloney Leukemia Virus into Midgestation Mouse Embryos. *Cell*, 1980; 19:181-188.
Gordon, et al., Production of Human Tissue Plasminogen Activator in Transgenic Mouse Milk. *BioTechnology*, 1987; 5:1183-1187.
Wilmut, et al., Method of Gene Transfer and Their Potential Use to Modify Milk Composition. Theriogenology, 1990; 33:113-123.
Rudolf Jaenisch, Germ line integration and Mendelian transmission of the exogenous Moloney leukemia virus. *PNAS USA*, 1976; 73:1260-1264.
Schiestl, et al., Integration of DNA fragments by illegitimate recombination in *Saccharomyces cerevisiae*. PNAS USA, 1991; 88:7585-7589.
Cibelli, et al., Transgenic Calves produced from Nonquiescent Fetal Fibroblasts. *Science*, 1998; 280:1256-1258.
Squirrell, et al., Long-term two-photon fluorescence imaging of mammalian embryos without compromising viability. *Nature BioTechnology* 1999; 17:763-767.
Hefzibah Eyal-Giladi, The Early Embryonic Development of the Chick, as an Epigenetic process. *Crit. Rev. Poultry Biol.* 1991; 3:143-166.
B.C. Wentworth, Fistulation Of The Hen's Oviduct. *Poultry Science* 1960; 39:782-785.
Pancer, et al., Recovery of Ova and their Re-Insertion into the Hen's Oviduct Through a Fistula. *British Poultry Science* 1989; 30:953-957.
Gilbert and Wood-Gush, A Technique for the Fistulation of the Hen's Oviduct Through the Abdominal Wall, With Recovery of the Ovum. *J. Reprod. Fertil.* 1963; 5:451-453.
Sang and Perry, Episomal Replication of Cloned DNA Injected Into the Fertillsed Ovum of the Hen,*Gallus domesticus*. *Mol. Reprod. Development* 1989; 1:98-106.

(Continued)

Primary Examiner—Michael C. Wilson
(74) Attorney, Agent, or Firm—Kyle D. Yesland

(57) ABSTRACT

The present invention provides for microinjection devices comprising a needle and a viewing instrument wherein the viewing instrument provides magnified viewing of an object to an operator from an angle other than a right angle to the object.

29 Claims, 6 Drawing Sheets

OTHER PUBLICATIONS

Love, et al., Transgenic Birds by DNA Microinjection. *BioTechnology.* 1994; 12:60-63.

Pain, et al., Chicken Embryonic Stem Cells and Transgenic Strategies. *Cells Tissues Organs,* 1999; 165:212-219.

Tanaka, et al., Chick production by in vitro fertilization of the fowl ovum. *J Reprod Fertil.* 1994, 100:447-449.

Korfiatis, Cell Synchronization for the Purpose of Nuclear Transfer in the Bovine.*Cloning and Stem Cells,* 2001; vol. 3, p. 125-138.

Vick, et al., Transgenic birds from transformed primordial germ cells. *Proc. R. Soc. Lond.,* 1993; vol. 251, p. 179-182.

Thoroval, et al., Germline transmission of exogenous genes in chickens using helper-free ecotropic avian leukosis virus-based vectors. *Transgenic Research,* 1995; vol. 4, p. 369-376.

Sayegh, et al., Avlan B cell development: lessons from transgenic models. *Vet. Immunology and Immunopathology,* 1999; vol. 72, p. 31-37.

Proudman, "The quest for transgenic poultry: birds are not mice with feathers" *Biotechnology in Animal Husbandry,* 2001; vol. 5, p. 283-299.

* cited by examiner

MICROINJECTION DEVICES AND METHODS OF USE

This application claims the benefit of U.S. provisional application No. 60/652,324, filed Feb. 11, 2005, the disclosure of which is incorporated in its entirety herein, and is a continuation-in-part of U.S. patent application Ser. No. 09/919,143, filed Jul. 31, 2001 now abandoned, the disclosure of which is incorporated in its entirety herein, which claims the benefit of U.S. provisional application No. 60/269,012, filed Feb. 13, 2001.

FIELD OF THE INVENTION

The invention provides for microinjection devices which facilitate the precise delivery of a substance to an object. The invention also provides for methods of using the devices.

BACKGROUND

The use of transgenic technology to introduce heterologous DNA into animals has been contemplated for the production of specific proteins or other substances of interest, such as proteins of pharmaceutical interest (Gordon et al., 1987, Biotechnology 5: 1183-1187; Wilmut et al., 1990, Theriogenology 33: 113-123). Transgenic animals can express exogenous proteins under conditions that offer high yield of the protein in an active form and can incorporate post-translational modifications such as glycosylation that are necessary for full functionality.

Historically, transgenic animals have been produced almost exclusively by microinjection of a fertilized egg. The pronuclei of fertilized eggs are microinjected in vitro with nucleic acid such as xenogeneic or allogeneic heterologous DNA or hybrid DNA molecules. The microinjected fertilized eggs are then transferred to the genital tract of a pseudopregnant female (see, for example, Krimpenfort et al., in U.S. Pat. Nos. 5,175,384, 5,434,340 and 5,591,669).

Systems that can function as protein bioreactors are reproductive systems which produce a hard shell egg such as the avian reproductive system. In avians the production of an egg begins with formation of the large yolk in the ovary. The unfertilized oocyte or ovum (i.e., germinal disc) is positioned on top of the yolk sac. Upon ovulation or release of the yolk from the ovary, it passes into the infundibulum of the oviduct where it is fertilized if sperm are present, and then moves into the magnum of the oviduct that is lined with tubular gland cells. These cells secrete the egg white proteins, including ovalbumin, lysozyme, ovomucoid, conalbumin and ovomucin, into the lumen of the magnum from which they are deposited onto the avian embryo and yolk.

The avian oviduct (for example, a chicken oviduct) offers outstanding potential as a protein bioreactor because of high levels of protein production, the promise of proper folding and post-translation modification of the recombinant protein, the ease of product recovery and the shorter developmental period of chickens compared to other potential transgenic species.

The use of retroviruses has proven to be the only dependable method of producing transgenic avians (see, for example, U.S. Pat. No. 6,730,822, issued May 4, 2004. However, the use of retroviruses, poses certain limitations, including limitations to the size of the transgene. The use of microinjection would overcome certain of these limitations.

Production of transgenic chickens by cytoplasmic DNA injection have been described in Sang et al, Mol. Reprod. Dev., 1: 98-106 (1989) and Love et al, Biotechnology, 12: 60-63 (1994) incorporated herein by reference in their entireties. However, to date, the production of transgenic chickens by means of DNA microinjection has been both inefficient and time consuming and has produced inconsistent results and a lack of germ-line transmission of the injected DNA. The problems associated with transgenic avian production by microinjection are believed to be due, at least in part, to the delicate structure of the fertilized or unfertilized germinal disc and the lack of devices and methods of manipulating the germinal disc.

What is needed, therefore, are devices and methods that provide for a micropipette (e.g., needle or injection needle) to be placed accurately and rapidly to a germinal disc for delivery of a substance such as nucleic acid component to the germinal disc.

SUMMARY OF THE INVENTION

The present invention provides for microinjection devices which facilitate the precise delivery of substances to an object such as a germinal disc. The invention also provides for methods of using such devices.

In one embodiment, the invention provides for a microinjection device which includes a needle and a viewing instrument. Typically, the viewing instrument provides for a magnified viewing of an object to an operator from an angle other than a right angle to the object. In one embodiment, the angle to the object is between about 1° and about 89°. For example, the angle to the object may be between about 10° and about 70°. In one embodiment, the angle for viewing the object is between about 30° and about 70°.

In one embodiment, the needle is an injection needle and the needle may be hollow. In addition, the needle may contain or consist of glass. In one useful embodiment, the needle includes a point or a bevel.

In one embodiment, the devices of the invention include a laser light source. The laser light source may be used to illuminate the needle, for example, the tip of the needle may be illuminated by the laser light source. In one embodiment, the laser light travels down the needle and illuminates the end of the needle, e.g., the bevel of the needle is illuminated. For example, the laser light source may be connected to the needle by a fiber optic line as seen in FIG. 1. Typically, the devices of the invention include an injector. The injector may be operably attached to the needle so as to facilitate the injection of a substance through the injection needle to an object such as a germinal disc. In one embodiment, the injector can provide for a reduced pressure in the injection needle thereby facilitating the drawing of a substance into the needle. The injector can also provide for a positive pressure which can facilitate the expulsion of a substance from the injection needle.

In one useful embodiment, devices of the invention include an oscillator. Typically, the oscillator is effective to impart an oscillation to the needle. In one embodiment, the oscillation of the needle includes an amplitude of between about 0.001 nm and about 100 μm.

Any useful viewing instrument may be employed in the present invention. In one embodiment, the viewing instrument includes a lens. For example, the viewing instrument may include a borescope.

The invention also provides for methods of using the devices of the invention. In one embodiment, the invention provides for viewing the surface of an object under magnification at an angle to a planar surface of the object of less than 90° (e.g., 20° to 80°) and injecting a substance to (e.g., into) the object through a needle. In one embodiment, the methods include viewing the surface of a germinal disc under magnification at an angle to the surface of the germinal disc of less than 90°, injecting a nucleic acid component into the germinal disc (e.g., a chicken germinal disc) through a needle; and allowing the germinal disc to develop into a chick.

In one embodiment, the invention provides for injecting a nucleic acid into a germinal disc by the micropipette wherein the micropipette or injection needle is inserted into the germinal disc. For example, the needle may be inserted into the germinal disc by penetrating a vitelline membrane and or and oolemma membrane. In one embodiment, the nucleic acid component is injected into a recipient cell of the germinal disc. The invention contemplates the delivery of the germinal disc to the oviduct of a recipient avian female, i.e., the delivery of the yolk containing the injected germinal disc to the oviduct of a recipient avian female.

In one embodiment, the nucleic acid component is a vector. For example, the vector may be a non-viral vector. In one embodiment, the nucleic acid sequence is an artificial chromosome.

In one specific embodiment, the invention comprises an optical microscope, a microinjection system and an oblique macro-monitoring unit for the microinjection of an avian ovum. The assembly or device of the present invention allows the operator to monitor the extent of the microinjection into an avian embryonic cell or cytoplast without interference from the optically opaque egg yolk.

In one aspect of the present invention, the microinjection system comprises a micromanipulator operably connected to a micropipette. The microscope may use transmitted light to monitor micropipette manipulation for filling the lumen thereof with a fluid, the fluid including a heterologous nucleic acid component which may include one or more of an isolated nucleic acid, a spermatozoon or an isolated cell nucleus. In one embodiment, the microscope includes an incident light beam in which an object such as an ovum is placed. In one embodiment, the relative position of the micropipette and the avian germinal disc of the ovum are monitored or viewed under magnification. Any component useful for viewing an object may be employed in the present invention. In one particular embodiment, a viewing instrument comprises a lens. The viewing instrument may also include a camera such as a video camera. In addition, the viewing instrument may include a video monitor.

Additional objects and aspects of the present invention will become more apparent upon review of the detailed description set forth below when taken in conjunction with the accompanying figures, which are briefly described as follows.

BRIEF DESCRIPTION OF THE DRAWINGS

In FIG. 2A, 79 represents an object viewed in accordance with the invention. In FIG. 2B, a germinal disc 70 atop a yolk 80 is shown wherein the germinal disc is viewed from other than perpendicular or 90° to the germinal disc (i.e., the perpendicular axis). For example, the viewing axis is from an angle between the perpendicular axis to the horizontal plane of the germinal disc and the horizontal plane of the germinal disc, as pointed out by the curved arrows.

FIG. 5A shows the micropipette (i.e., injection needle) positioned over the vitelline membrane of an avian ovum and over the underlying germinal disc. FIG. 5B illustrates the indentation of the vitelline membrane of an avian ovum by depressing the micropipette. FIG. 5C illustrates the insertion of a micropipette into the germinal disc of an avian ovum after penetrating the vitelline membrane.

DETAILED DESCRIPTION OF THE INVENTION

Figure 1:
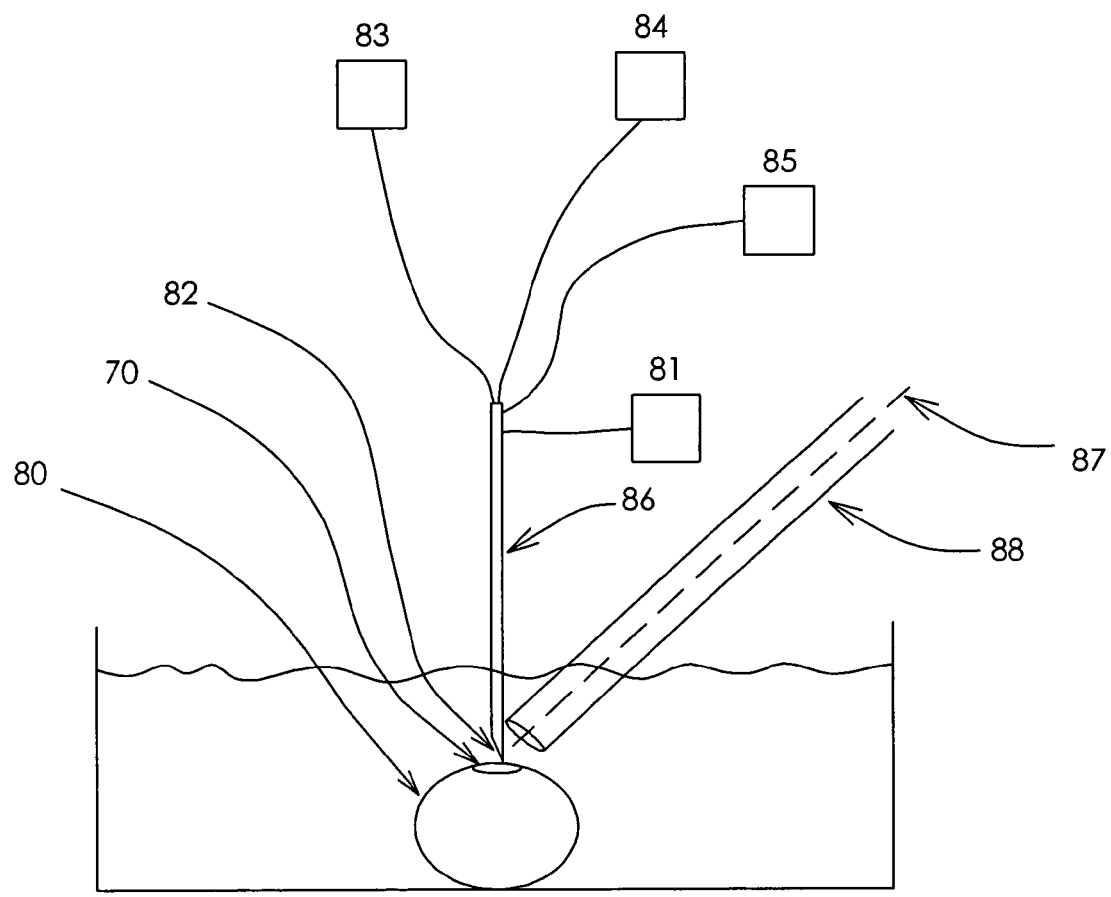
FIG. 1 illustrates one embodiment of the invention. 70 represents the germinal disc sitting atop a yolk 80 in a container of Ringer's buffer; 83 represents a fiber optic laser light source; 84 represents an injector system; 85 represents a piezo oscillation source; 81 represents a micromanipulator operably attached to the needle; 86 represents an injection needle; 82 represents a bevel of the injection needle; 87 represents a viewing axis; and 88 represents a component which provides for a magnified viewing, for example, a borescope.

For convenience, certain terms employed in the specification, examples, and appended claims are collected here.

Definitions

The term "animal" as used herein refers to all vertebrate animals, including birds. It also includes an individual animal in all stages of development, including embryonic and fetal stages.

The term "avian" as used herein refers to any species, subspecies or race of organism of the taxonomic class aves, such as, but not limited to, chicken, turkey, duck, goose, quail, pheasants, parrots, finches, hawks, crows and ratites including ostrich, emu and cassowary. The term includes the various know strains of Gallus gallus, or chickens, (for example, White Leghorn, Brown Leghorn, Barred-Rock, Sussex, New Hampshire, Rhode Island, Ausstralorp, Minorca, Amrox, California Gray, Italian Partidge-colored), as well as strains of turkeys, pheasants, quails, duck, ostriches and other poultry commonly bred in commercial quantities.

The term "germinal disc" as used herein refers to an unfertilized or fertilized ovum. The "germinal disc," therefore, may be a single cell prior to fertilization or a multicellular blastodisc after fertilization. The germinal disc is visible at the surface of the yolk of an egg. In particular, the germinal disc, as used herein, refers to the white disc located at the surface of the yolk containing a fertilized or unfertilized egg.

The term "blastoderm" as used herein refers to the avian embryonic stage wherein the area pellucida is complete (Stage X), the blastodermal cell layer being detached from the underlying yolk.

The term "Stage X embryo" as used herein refers to the blastodermal stage of the avian embryonic developmental cycle at the point where the hard-shell egg is laid. Ovulation in the chicken occurs 20-30 minutes after the laying of an egg. The ovum comprises a large optically opaque yolk, on top of which is a 2-3 mm diameter germinal disc.

The term "micromanipulator" as used herein refers to an instrument which can provide for a controlled and precise movement of an implement. For example, a micromanipulator can provide for movement and positioning of an injection needle.

The terms "ovum" and "oocyte" are used interchangeably herein. Although only one ovum matures at a time, an animal is born with a finite number of ova. In avian species, such as a chicken, ovulation, which is the shedding of an egg from the ovarian follicle, occurs when the brain's pituitary gland releases a luteinizing hormone, LH. After ovulation, the ovum enters the infundibulum where fertilization occurs. Fertilization must take place within 15 minutes of ovulation, before the ovum becomes covered by albumen. During fertilization, sperm (avians have polyspermic fertilization) penetrate the germinal disc where the embryo will develop. When the sperm lodges within this germinal disc, an embryo begins to form. After fertilization, the ovum is known as a "blastoderm" or "zygote." After fertilization, the ovum is known as a "blastoderm" or "zygote". The fertilized ovum descends the oviduct where the outer albumen and the shell membranes are deposited around the ovum. The hard shell is deposited once the ovum has reached the uterus. In the uterus, rotation of the egg governs the orientation of the embryo in the egg. See Eyal-Giladi, 1991, Revs. Poultry Biol. 3: 143-166, incorporated herein by reference in its entirety.

The zygote (germinal disc) begins to cleave upon entering the uterus, with a series of 5-6 divisions over a two-hour period, whereupon the central cells detach from the underlying yolk. The space between the cells and the yolk is the sub-blastodermic cavity. After about 11 hours, the germinal disc is a 5-6 cell thick blastoderm (Stage V of development). In the succeeding Stages VII-X, the cells closest to the yolk slough and fall to the yolk surface (Stage VIII) to leave a one-cell thick layer in the center of the blastoderm, the area pellucida (Stage X), whereupon the egg is laid. At Stage X, the blastoderm has predestined anterior and posterior ends for the developing embryo.

The terms "gene" or "genes" as used herein refer to nucleic acid sequences (including both RNA and DNA) that encode genetic information for the synthesis of a whole RNA, a whole protein, or any portion of such whole RNA or whole protein. Genes that are not naturally part of a particular organism's genome are referred to as "foreign genes," "heterologous genes" or "exogenous genes" and genes that are naturally a part of a particular organism's genome are referred to as "endogenous genes." The term "gene product" refers to RNAs or proteins that are encoded by the gene. "Foreign gene products" are RNA or proteins encoded by foreign genes and "endogenous gene products" are RNA or proteins encoded by endogenous genes. "Heterologous gene products" are RNAs or proteins encoded by foreign, heterologous genes and that, therefore, are not naturally expressed in the cell.

The term "nucleic acid" as used herein refers to any natural or synthetic linear or sequential array of nucleotides and/or nucleosides, for example cDNA, genomic DNA, mRNA, tRNA, oligonucleotides, oligonucleosides and derivatives thereof. For ease of discussion, nucleic acids referred to herein include, without limitation, "constructs," "plasmids," or "vectors." Representative examples of nucleic acids include expression vectors, cloning vectors, cosmids, artificial chromosomes such as YACs, BACs and mammalian artificial chromosomes (MACs) animal viral vectors such as, but not limited to, modified adenovirus, influenza virus, adeno-associated virus, polio virus, pox virus, retrovirus, and the like, vectors derived from bacteriophage nucleic acid, and synthetic oligonucleotides such as chemically synthesized DNA or RNA. Nucleic acids may include modified or derivatised nucleotides and nucleosides such as, but not limited to, halogenated nucleotides such as, but not only, 5-bromouracil, and derivatised nucleotides such as biotin-labeled nucleotides.

The term "isolated nucleic acid" as used herein can refer to a nucleic acid with a structure (a) not identical to that of any naturally occurring nucleic acid or (b) not identical to that of any fragment of a naturally occurring genomic nucleic acid spanning more than three separate genes, and includes DNA, RNA, or derivatives or variants thereof. The term covers, for example, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, i.e., a gene encoding a fusion protein, and (e) a recombinant nucleotide sequence that is part of a hybrid sequence that is not naturally occurring. An isolated nucleic acid can also refer to a nucleic acid molecule that is substantially purified or is not present in the biochemical environment native (as found in nature) to the nucleic acid.

The term "fragment" as used in reference to a nucleic acid (e.g., cDNA) refers to an isolated portion of the subject nucleic acid constructed artificially (e.g., by chemical synthesis) or by cleaving a natural product into pieces, for example, by using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art. The term "fragment" as used herein may also refer to an isolated portion of a polypeptide, wherein the portion of the polypeptide is cleaved from a naturally occurring polypeptide, for example, by proteolytic cleavage by at least one protease, or is a portion of the naturally occurring polypeptide produced by methods well known to one of skill in the art.

The terms "nucleic acid vector" or "vector" as used herein refer to a natural or synthetic single or double stranded nucleic acid molecules that can be transfected or transformed into cells and replicate independently of, or within, the host cell genome.

The term "cytoplast" as used herein refers to a chromosome-free recipient cell, wherein chromosomal removal is referred to as enucleation when the nucleus or chromosomes (e.g., organized in a metaphase plate) of a cell are removed or destroyed.

The term "recombinant cell" refers to a cell that has a new combination of nucleic acids not present in nature. A new combination of nucleic acid segments can be introduced into an organism using a wide array of nucleic acid manipulation techniques available to those skilled in the art. The recombinant cell can harbor a vector that is extragenomic. An extragenomic nucleic acid vector does not insert into the cell's genome. A recombinant cell can further harbor a vector or a portion thereof that is intragenomic. The term "intragenomic" defines a nucleic acid incorporated within the recombinant cell's genome.

The term "recombinant nucleic acid" as used herein refers to combinations of at least two nucleic acid sequences that are not naturally found in a eukaryotic or prokaryotic cell. The nucleic acid sequences may include, but are not limited to nucleic acid vectors, gene expression regulatory elements, origins of replication, sequences that when expressed confer antibiotic resistance, and protein-encoding sequences. The term "recombinant polypeptide" is meant to include polypeptides produced by recombinant DNA techniques such that it is distinct from a naturally occurring polypeptide either in its location, purity or structure. Generally, a recombinant polypeptide will be present in a cell in an amount different from that normally observed in nature.

The term "male germ cells" as used herein refers to spermatozoa (i.e., male gametes) and developmental precursors thereof. In the sexually mature male vertebrate animal, there are several types of cells that are precursors of spermatozoa, which can be genetically modified, including the primitive spermatogonial stem cells, known as A0/As, which differentiate into type B spermatogonia. The latter further differentiate to form primary spermatocytes, and enter a prolonged meiotic prophase during which homologous chromosomes pair and recombine. Useful precursor cells at several morphological/developmental stages are also distinguishable: preleptotene spermatocytes, leptotene spermatocytes, zygotene spermatocytes, pachytene spermatocytes, secondary, spermatocytes, and the haploid spermatids. The latter undergo further morphological changes during spermatogenesis, including the reshaping of their nucleus, the formation of acrosome, and assembly of the tail. The final changes in the spermatozoa (i.e., male gamete) take place in the genital tract of the female, prior to fertilization.

The term "transgenic animal" as used herein refers to any avian species, including, but not limited to, the chicken, in which one or more of the cells of the bird contain heterologous nucleic acid introduced by way of human intervention, such as by transgenic techniques disclosed herein. The nucleic acid is introduced into a cell, directly or indirectly by introduction into a precursor of the cell, by way of deliberate genetic manipulation, such as by sperm-mediated or restriction-enzyme mediated integration, microinjection or by infection with a recombinant virus. The term "genetic manipulation" does not include classical cross-breeding, or in vitro fertilization, but rather is directed to the introduction of a nucleic acid. The nucleic acid may be integrated within a chromosome, or it may be extrachromosomally replicating DNA. In the typical transgenic animal, the transgene causes cells to express a recombinant form of a pharmaceutical protein, for example, and without limitation, an immunoglobulin polypeptide or a variant polypeptide thereof.

"Transchromosomic avian" means an avian which contains an artificial chromosome in some or all of its cells. A transchromosomic avian can include the artificial chromosome in its germ cells.

As used herein, the term "transgene" means a nucleic acid sequence that is partly or entirely heterologous, i.e., foreign, to the transgenic animal or cell into which it is introduced, or, is homologous to an endogenous nucleic acid sequence of the transgenic animal or cell into which it is introduced but is introduced at site in the genome where the nucleic acid is not normally present. For example, the transgene may be designed to be inserted, or is inserted, into the animal's genome in such a way as to alter the genome of the cell into which it is inserted (e.g., it is inserted at a location which differs from that of the natural gene or its insertion results in a knockout). A transgene can include one or more coding sequences and one or more gene expression regulatory sequences such as transcriptional regulatory sequences and any other nucleic acid, such as introns, that may be useful for expression of a selected nucleic acid.

The term "donor cell" as used herein refers to the source of the nuclear structure that is transplanted to the recipient enucleated cytoplast. All cells of normal karyotype, including embryonic, fetal, and adult somatic cells may be nuclear donors. The use of non-quiescent cells as nuclear donors has been described by Cibelli et al., (1998, Science 280: 1256-8).

The term "recipient cell" as used herein refers to an enucleated recipient cell, preferably an enucleated metaphase I or II oocyte an enucleated preactivated oocyte or a pronuclear stage egg. Enucleation may be accomplished by splitting the cell into halves, aspirating the metaphase plate, pronucleus or pronuclei, or even by irradiation. Enucleation may be done through two-photon laser-mediated ablation. TPLSM could be used to guide mechanical enucleation.

The term "TPLSM" as used herein refers to two-photon laser scanning microscopy. TPLSM is based on two-photon excited fluorescence in which two photons collide simultaneously with a fluorescent molecule. Their combined energy is absorbed by the fluorophore, inducing fluorescent emission, detected by a photomultiplier tube and converted into a digital image (See Squirrell et al, 1999, Nature Biotechnol. 17: 763-7 and Piston et al., 1999, Trends Cell Biol. 9: 66-9). TPLSM allows for the generation of images of living, optically dense structures for prolonged periods of time, while not affecting their viability. TPLSM can use biologically innocuous pulsed near-infrared light, usually at a wavelength of about 700 nm to about 1000 nm, which is able to penetrate deep into light-scattering specimens. TPLSM may employ different lasers, such as a mode-locked laser, where the wavelength is fixed, or a tunable laser that can be tuned to wavelengths between about 700 nm and about 1000 nm, depending upon the range of emission of the dye used. For DAPI and Hoescht 33342 dyes, 750-830 nm is suitable. New fluorophores are being produced with different ranges of emission and the invention is not limited to the presently available dyes and their respective emission ranges. Furthermore, lasers used in TPLSM can be grouped into femtosecond and picosecond lasers. These lasers are distinguished by their pulse duration. A femtosecond laser is preferred since it is particularly suitable for visualization without harming the specimen.

A "needle" includes in its meaning an "injection needle" which as used herein includes in its meaning the term micropipette as used herein. An injection needle is an object which can be cylindrical in shape and through which a fluid such as a fluid containing a biological substance (e.g., a fluid containing a nucleic acid component) can be passed for the precise delivery of the fluid to an object.

Figure 3:
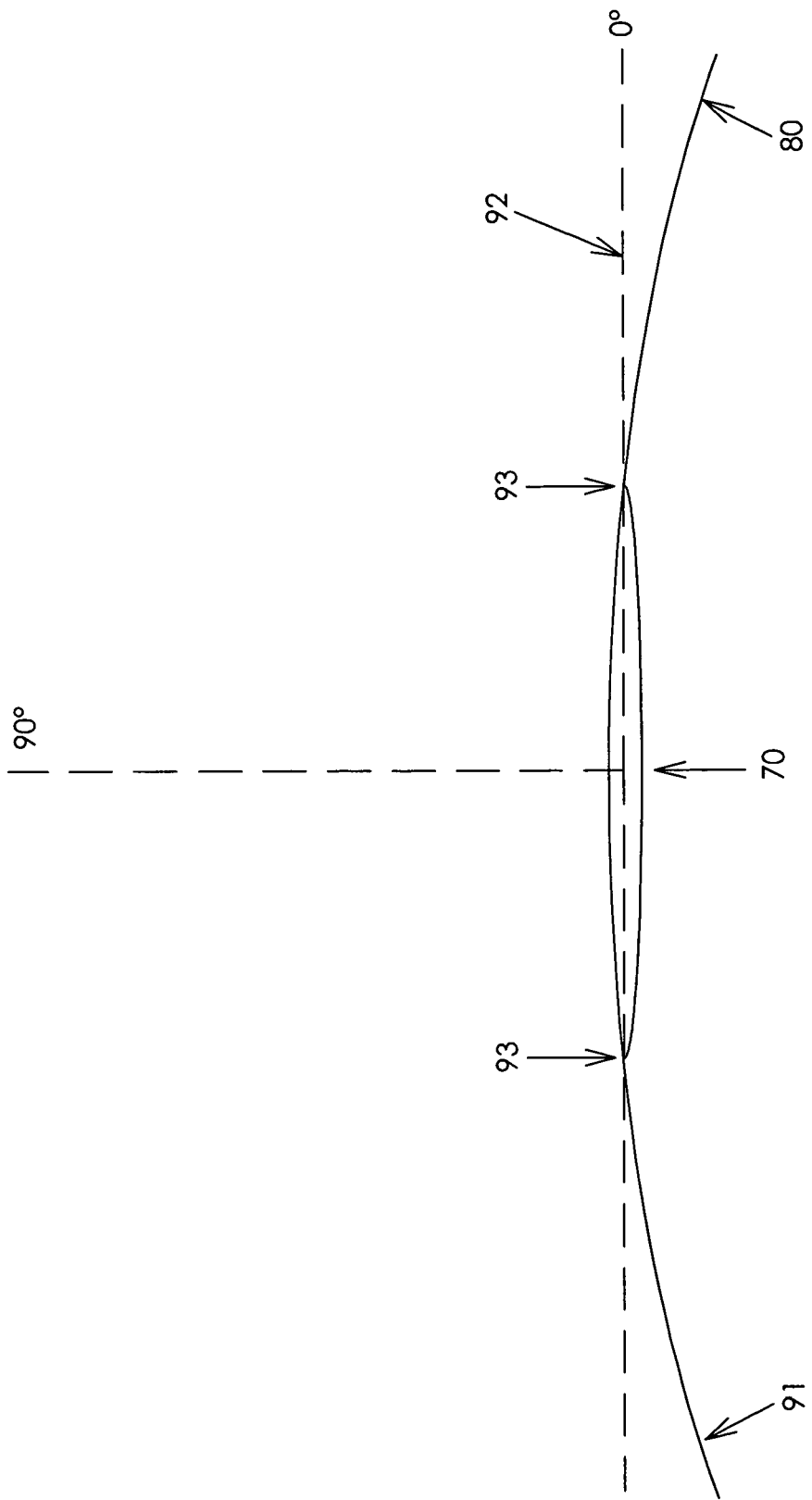
FIG. 3 illustrates a perpendicular axis (i.e., a 90° angle) of a germinal disc. 91 represents a vitelline membrane; 70 represents a germinal disc; and 92 is a horizontal axis passing through the distal (outer most) edges of the germinal disc at points 93. The perpendicular axis of the germinal disc is at a 90° angle to the horizontal axis of the germinal disc.

A "planar surface" of an object is delineated by a plane which bisects points of the perimeter of the object. FIG. 3 shows a planar surface of a germinal disc.

"Perpendicular" means being at a right angle to a plane. An "oblique angle" means an angle which is neither perpendicular nor parallel to a plane.

A "viewing instrument" is an implement which can enhance the visualization of an object, for example, by magnification.

A "nucleic acid component" is a substance, such as a fluid, or an object, such as a chromosome (e.g., an artificial chromosome), which comprises a nucleic acid.

Abbreviations

Abbreviations used in the present specification include the following: cDNA, DNA complementary to RNA; mRNA, messenger RNA; tRNA, transfer RNA; nt, nucleotide(s); μm, micrometer; μM, micromolar; ml, milliliter; μl, microliter; nl, nanoliter; h, hours; min, minutes; TPLSM, two photon laser scanning microscopy; REMI, restriction enzyme mediated integration.

The invention provides for microinjection devices which facilitate the precise delivery of a substance to an object. The invention also provides for methods of using the devices. In one embodiment, the invention provides for methods and devices which allow for the precise delivery of a substance such as a fluid containing nucleic acid to a germinal disc, for example, to produce a transgenic (e.g., transchromosomic) avian.

In one embodiment, the microinjection devices comprise a needle capable of introducing a substance into (or onto) an object. Typically, the needle is an elongated and pointed implement which can pierce the outer boundary of the object (e.g., membrane) and introduce the substance into the object. In one embodiment, the substance is present on the needle. In another embodiment, the needle is hollow and the substance is present inside the needle. In one particularly useful embodiment, the substance is injected through the needle. The needle may comprise any useful material such as, at least one of, metal or glass material. In one useful embodiment, the needle is a drawn out glass tube such as a capillary tube. For example, a glass capillary tube may be heated and pulled to create a thin glass needle.

In a particularly useful embodiment, the needle includes a bevel shape. The bevel may be of any useful size and may have any useful angle. In one embodiment, the bevel of the needle is between about 20 μm to about 30 μm in length and has approximately a 60° bevel angle. A needle having a bevel angle of about 60° can be seen in FIG. 4. Typically, the angle of the bevel is such to facilitate entry of the needle into the object. However, in one embodiment, a needle useful as disclosed herein does not require a bevel.

The invention contemplates the employment of any useful method for determining the depth the needle penetrates into the object. In one useful embodiment of the invention, creating a bevel of an approximate length allows the microinjection device operator to visualize the depth of the needle in the object by using the size of the bevel for reference. For example, the depth of the bevel can be visualized inside the ooplasm of an egg. In one embodiment, when the upper part of the bevel is visualized just above the egg's vitelline membrane the depth of penetration of the needle will be known based on the length of the bevel (see FIG. 4). In another embodiment, the needle is marked with a scale that is useful for showing the depth of penetration of the needle. Depth determination is particularly useful when inserting a needle into delicate objects such as a germinal disc wherein the depth of penetration and disruption of internal matter should preferably or requisitely be kept to a minimum. The invention is not limited to any particular depth of penetration into a germinal disc (i.e., into the oolemma membrane); however, one useful range of depth penetration is between about 5 μm and about 50 μm.

In one embodiment, the microinjection device provides a source for illumination of at least a portion of the needle thereby enhancing visualization of the needle, for example, enhancing visualization of the bevel of the needle. In one particularly useful embodiment, the illuminated needle comprises glass. In one embodiment, the illumination is provided by a laser light source. In one embodiment, the laser light source provides light in the visible range of relatively long wavelength thereby reducing opportunity for cellular damage to be induced by the light. For example, and without limitation, the laser light can be red light. In one embodiment, the source of illumination is above the needle such that light (e.g., laser light) travels down the needle and illuminates the end (e.g., bevel) of the needle. In one embodiment, the laser light is delivered to the needle by a fiber optic line. That is, laser light can be delivered to the needle by a fiber optic line, and thereafter the light is transmitted down the needle resulting in an illumination of the end of the needle (see FIG. 1) providing for an enhanced visualization of the tip (e.g., bevel) of the needle against the backdrop of, for example, the yolk of an egg. In one certain and nonlimiting embodiment, a 635 nm/25 mW laser (Coherent Radius 635-25) laser light source is used to illuminate the needle providing a color contrast between the tip of the needle with the surface of the yolk and other surroundings.

Typically, in instances where a hollow needle is used, the microinjection device includes an injector system. In one embodiment, the injector system is effective to facilitate the injection of the substance through the needle into the object (for example, see FIG. 1). Any useful injector system known to those of skill in the art may be used in the present invention. In one useful embodiment, the injector system is a pico-injector system (Harvard Apparatus PLI-100).

Any useful instrument which can provide for an enhanced viewing of the object and thereby facilitate the microinjection process is contemplated for use in the present invention. Typically, an instrument employed for viewing comprises a magnifier. That is, the viewing instrument provides for a magnified view of the object. Any useful magnifier can be employed in the present invention. Typically, the magnifier will comprise a lens. Any useful magnification power may be used in the invention. That is, any magnification power which will provide for an enhanced viewing of the object, relative to viewing the object without magnification, is within the scope of the present invention. For example, and without limitation, a magnification of between about 2× and about 20,000× may be used. In one embodiment, a magnification of between about 5× and about 2,000× is used. For example, a magnification of about 10× to about 200× may be used. In one certain embodiment, a magnification of about 70× (e.g., 71.6×) is used.

Figure 2A:
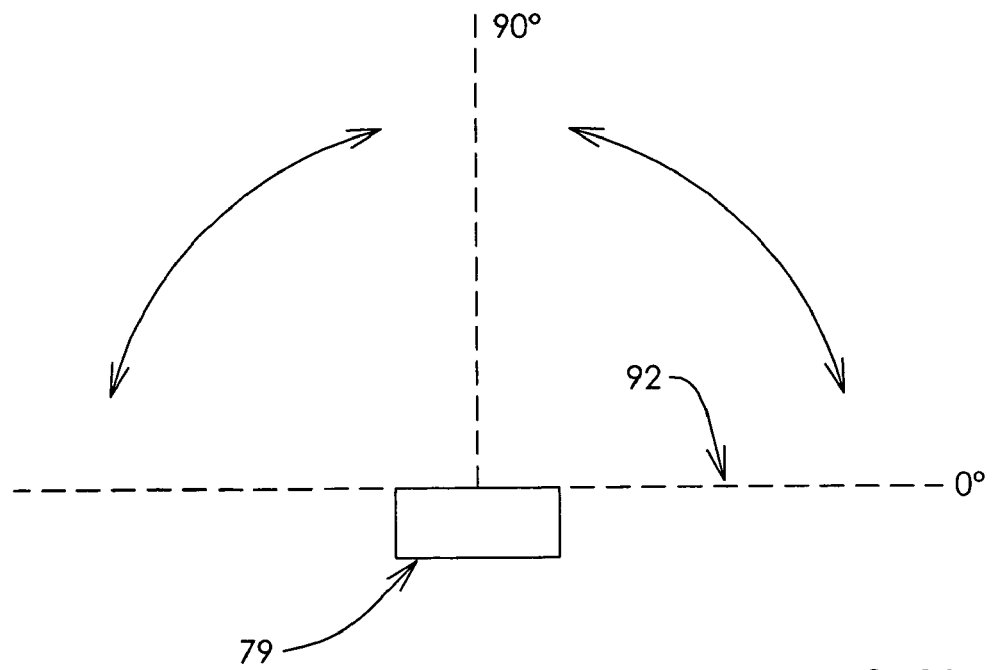
FIGS. 2A and 2B illustrate viewing angles which may be employed in the present invention. The figure shows viewing angles other than directly above the object or germinal disc (i.e., not perpendicular to the plane or horizontal axis 92 of the object or germinal disc) in accordance with the present invention, as pointed out by the curved arrows.
Figure 2B:
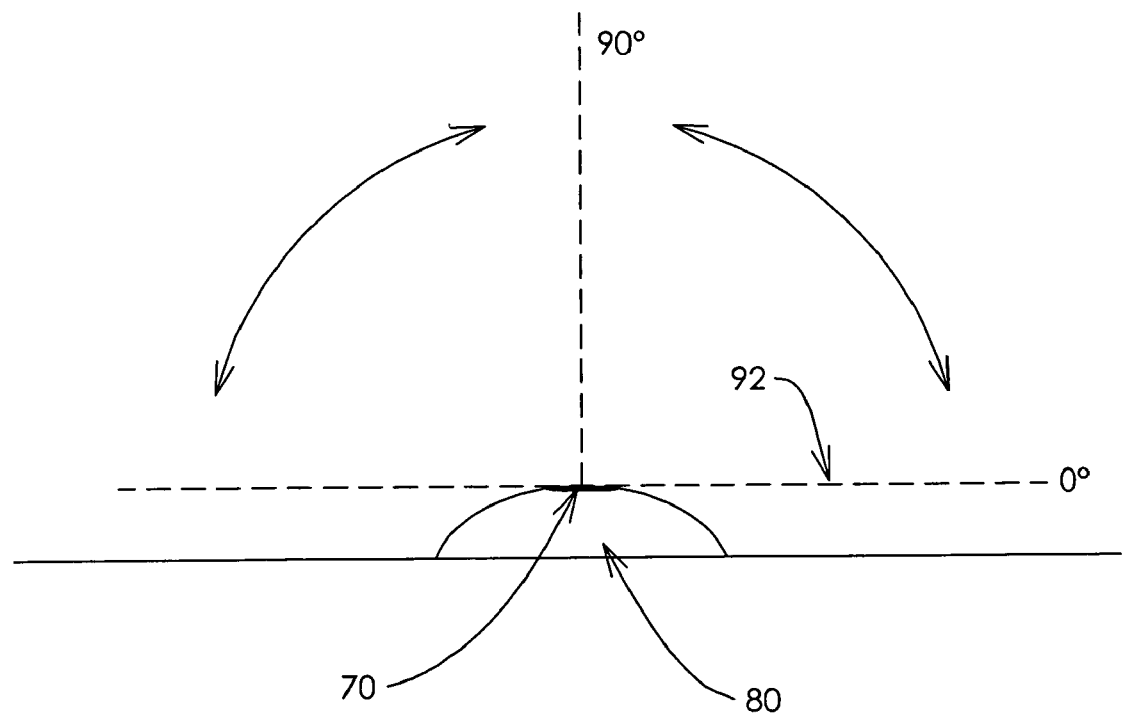

One particularly useful aspect of the invention is the feature of viewing or monitoring the object, for example, a germinal disc, from a position other than directly above (i.e., other than perpendicular to or at a right angle to) the object (FIG. 2). For example, the object may be viewed (i.e., the axis of viewing may be) at an angle in a range of about 1° to about 89° relative to the planar surface of the object. For example, the object may be viewed at an angle of about 89° or at an angle of about 85° or at an angle of about 80° or at an angle of about 75° or at an angle of about 70° or at an angle of about 65° or at an angle of about 60° or at an angle of about 55° or at an angle of about 50° or at an angle of about 45° or at an angle of about 40° or at an angle of about 35° or at an angle of about 30° or at an angle of about 25° or at an angle of about 20° or at an angle of about 15° or at an angle of about 10° or at an angle of about 5° or at an angle of about 1°. In one useful embodiment, the object is viewed at an angle of about 1° to about 85° relative to the planar surface of the object (e.g., about 1° to about 80°). For example, the object may be viewed at an angle of about 1° to about 75° (e.g., about 1° to a about 70°). In one useful embodiment, the object is viewed from an angle of about 2° to about 60° for example, about 5° to about 50° (e.g., about 10° to about 40°). In one particularly useful embodiment, the object is viewed from an angle of about 20° to about 50° for example, about 30° to about 40° (e.g., about 32 to about 34°).

The viewing of the object from a position other than perpendicular to the object is particularly useful for visualizing a germinal disc present on (e.g., atop) a yolk of an egg (e.g., an avian egg). For example, the opaque yolk of an egg can substantially obscure the germinal disc making depth perception in the disc difficult or impossible.

In one particularly useful embodiment, the object is a germinal disc. A germinal disc is an essentially circular object that comprises a substantially flat surface to which a perpendicular axis can be delineated. For example, a horizontal plane may be established which bisects the outer edge or edges of a germinal disc. See FIG. 3 which shows a side view of a germinal disc atop a yolk. A perpendicular line extended from the center of the horizontal plane of the germinal disc will provide a 90° angle from the germinal disc. In accordance with the present invention, the viewing angle of the germinal disc is less than 90° (see FIG. 2 and FIG. 3).

In one particular embodiment of the invention, the viewing or imaging component of the device includes a microscope such as a borescope. In one embodiment, all or a portion of the object is submersed in fluid (e.g., Ringer's solution). In one embodiment, all or a portion of the viewing mechanism is submersed in fluid. In one particular embodiment, a 6 mm diameter submersible borescope is used which may be partially submersed in fluid. See FIG. 1.

In one particularly useful aspect, the invention comprises one or more micromanipulators. Typically, although not exclusively, all or part of the viewing instrument can be positioned (i.e., moved to a certain location) by employing a micromanipulator operably attached to the all or part of the viewing instrument. The micromanipulator may provide movement of the all or part of the viewing instrument on one or more axes. In one certain embodiment, the viewing instrument is a borescope which is mounted on a heavy-duty micromanipulator (Siskiyou Design Instruments Inc, catalogue # MX1640) which provides for positioning of the borescope by movement on each of three independent axes.

In one useful embodiment, the needle can be positioned (i.e., moved to a certain location) by employing a micromanipulator operably attached to the needle. The invention contemplates the movement of the needle provided by the micromanipulator to be in one, two or three axes. That is, the needle can be placed at any position on the object and can be moved to pierce the object. In addition, the needle can be placed at an angle relative to the object.

Figure 4A:
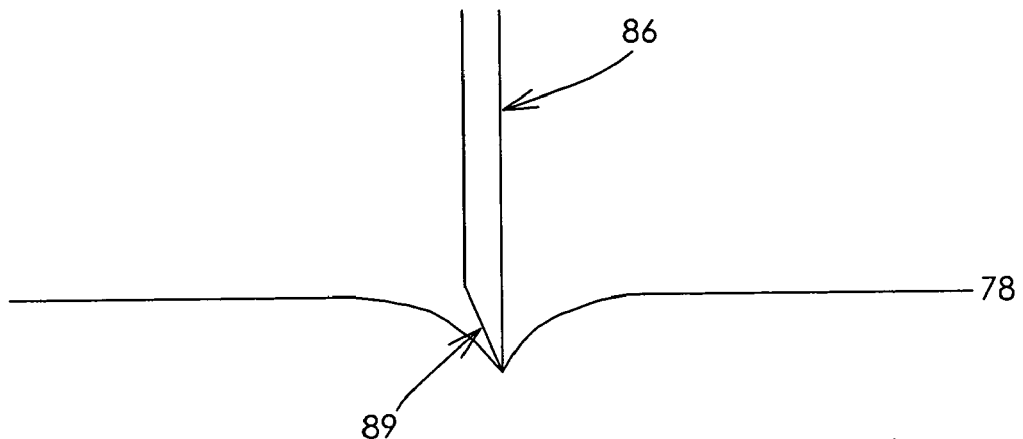
FIG. 4A illustrates the injection needle 86 indenting the oolemma membrane 78 so that the top of the bevel 89 of the injection needle 86 is still visible above the membrane surface.

In one embodiment, the microinjection device includes a piezo unit. Typically, the piezo unit is operably attached to the needle to impart oscillations to the needle. However, any configuration of the piezo unit which can impart oscillations to the needle is included within the scope of the invention. In certain instances the piezo unit can assist the needle in passing into the object. For example, the avian oolemma (plasma membrane of an avian embryo) is significantly more flexible and elastic than the mammalian counterpart. In certain instances this flexibility can result in the formation of a depression in the oolemma at the point of contact between the oolemma and the tip of the needle as the needle moves into the germinal disc (FIG. 4A). Eventually, the membrane is pierced and the pipette penetrates the egg. However, this can result in the deep impalement of the germinal disk, causing significant mechanical stress to the embryo, for example, damage to the nucleus and/or other components of the germinal disc. The use of at least one commercially available piezo drill system, developed for the micromanipulation of mammalian eggs (Perry et al (1999) Science 284: 1180-1183), appears to not significantly reduce the depth of the depression of the oolemma before piercing during injection of avian stage I embryos.

Figure 4B:
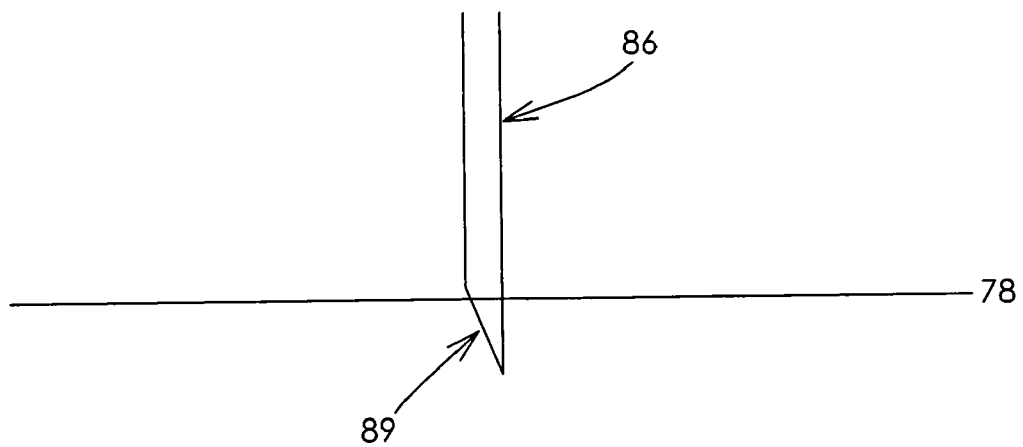
FIG. 4B illustrates the injection needle after passing into the oolemma membrane 78 so that the top of the bevel 89 of the needle is still visible above the membrane surface.

To overcome the problem of impalement of the germinal disc, in one embodiment, the microinjection device includes a specifically designed tunable "piezo drill" unit that provides for an oscillating movement of the needle at a frequency substantially higher than certain other piezo drills such as those used for microinjection into mammalian embryos. This rapid movement can permit the needle to pass through the membrane in a manner that provides for reduced or eliminated damage to the germinal disc. For example, the needle can be positioned such that a slight dimple is formed in a membrane (FIG. 4A). The piezo is activated, thereby allowing only a small portion of the needle (e.g., the bevel) to pass through the membrane before injection (FIG. 4B). The "piezo drill" also provides for a tunable frequency and amplitude which provides for optimization of the piezo's performance (e.g., passage of the needle into the object, i.e., into a germinal disc).

The oscillations of the needle imparted by the piezo may be in any useful direction. For example, and without limitation, the oscillations may be sided to side, back and forth, up and down, in circular, oval, square, rectangular motions or other patterns or combinations thereof. In one useful embodiment, the oscillations are side to side.

In one embodiment, the piezo unit is operably attached to the needle meaning the piezo unit is able to impart oscillations to the needle. In one embodiment, the piezo unit is activated during the penetration of the oolemma by the needle. For example, the needle may be a piezo electrically-driven needle, i.e., the needle punctures the surface of the object (e.g., oolemma) in a manner facilitated (e.g., substantially facilitated) by the action of the piezo unit.

The invention contemplates the employment of any useful frequency of oscillations imparted to the needle by the piezo. In one embodiment, a frequency of greater than 100 Hz is used. The invention contemplates the upper limit for frequency as being limited by the mechanics of the piezo. For example, and without limitation, a frequency of between about 100 Hz and about 100,000 kHz is within the scope of the invention. In one useful embodiment, the frequency is between about 100 Hz and about 100 kHz, for example, about 500 Hz and about 50 kHz. In one embodiment, the frequency is between about 500 Hz and about 10 kHz, for example, about 500 to about 5 kHz. In one certain embodiment, the frequency is about 3100 Hz.

The invention contemplates the employment of any useful amplitude of oscillations imparted to the needle by the piezo. For example, the travel distance of the needle is contemplated as being between about 0.001 nm and about 100 µm. In one embodiment, the travel distance of the needle is between about 0.1 nm and about 50 µm. In one embodiment, the travel distance of the needle is about 1 nm to about 20 µm or about 1 nm to about 10 µm. In one useful embodiment, the travel distance of the needle is about 0.01 µm to about 20 µm. In one particularly useful embodiment, the travel distance of the needle is about 0.1 µm to about 20 µm, for example, about 1.0 µm to about 10 µm (e.g., 5 µm or 7.5 µm).

In one particular embodiment, the piezo unit includes one or more of, for example, all of: a Signal Generator (BK Precision Model # 4011A) set to operate at a frequency of 5 KHz; an Amplifier (Physik Instrumente GmbH, Amplifier: PI-Polytec E-505 PZT-Power Amplifier, Average power 30 W, output voltage −20 to +120 V and optimized for 100V PiezoDrive); and a Piezo actuator (Physik Instrumente GmbH, catalog # P-840.10, 5 µm travel for latitudinal vibration).

The needle may approach the object from any useful angle. In one particularly useful embodiment, the longitudinal axis of the needle is visible when viewing the object. That is, the viewing instrument is not placed directly above the needle (i.e., the viewing axis is not parallel to the longitudinal axis of the needle). See FIG. 1.

The invention contemplates the delivery of any useful substance to an object. In a particularly useful embodiment, the invention provides for the delivery of an aqueous solution to an object. In one embodiment, the aqueous solution includes a biomolecule such as nucleic acid (e.g., DNA or RNA) or nucleic acid component. Any useful type of nucleic acid may be employed in the present invention. For example, the nucleic acid may be linear or (e.g., coiled or uncoiled), circular (e.g., open circular or closed circular). In one embodiment, the nucleic acid is associated with protein, for example, a chromosome (e.g., an artificial chromosome) may be delivered to an object. The invention also contemplates the delivery of a nucleus to an object. In one embodiment, "delivery" means introducing into, for example, inside of an object such as a germinal disc.

The object to which the substance is delivered in accordance with the present invention may be any object for which it is advantageous to deliver a substance to the object as disclosed herein. In one embodiment, the object is a biological object. For example, the object may comprise one or more cells. The one or more cells may be nucleated or anucleated. In one embodiment, the object is an ovum or an embryo. In one particularly useful embodiment, the object is a germinal disc, for example, a fertilized germinal disc.

In one embodiment, the present invention is useful to create a transgenic (e.g., transchromosomic, avian by injecting a nucleic acid component (e.g., an artificial chromosome, see, for example, U.S. patent application Ser. No. 11/068,155, filed Feb. 28, 2005, now abandoned, the disclosure of which is incorporated in its entirety herein by reference) into an avian reproductive cell such as a germinal disc which is atop a yolk. In one embodiment, the invention provides for a minimally invasive delivery of DNA or other substance to a germinal disc thereby providing for a germinal disc which remains viable after injection.

To produce a transgenic avian, a fertilized ova (stage I embryo) is isolated from a euthanized hen (female bird), for example, 45 min to 4 h after oviposition of the previous egg. Alternatively, the eggs can be isolated from hens whose oviducts have been fistulated according to the techniques of Gilbert & Wood-Gush, J. Reprod. Fertil., 5: 451-453 (1963) and Pancer et al, Br. Poult. Sci., 30: 953-7 (1989), each incorporated by reference herein in their entireties.

In one embodiment, the yolk is placed in a dish with the germinal disc upwards. Ringer's buffer medium can be added to the dish to prevent drying. The microinjection device shown in FIG. 1 is used to inject the nucleic acid component into the germinal disc by positioning of the germinal disc under the viewing instrument and guiding the injection needle of the device into the germinal disc until a dimple is formed in the oolemma to a useful depth, for example, to a depth of less than 20 µm. The piezo unit is then activated for a period of time sufficient for the needle to penetrate the oolemma. Penetration of the needle through the oolemma can readily be visualized through the viewing instrument. After the needle has penetrated the oolemma, the injector system is activated thereby injecting a nucleic acid component into the germinal disc.

Injected embryos are then surgically transferred to a recipient hen as described, for example, in Olsen & Neher, J. Exp. Zool., 109: 355-66 (1948) and Tanaka et al, J. Reprod. Fertil., 100: 447-449 (1994). In one embodiment, the injected embryos are surgically transferred to recipient hens via the ovum transfer method of Christmann et al in PCT/US01/26723, published Aug. 27, 2001, the disclosure of which is incorporated herein by reference in its entirety, and hard shell eggs are incubated and hatched. The embryo is allowed to proceed through the natural in vivo cycle of albumin deposition and hard-shell formation. The transgenic embryo is then laid as a hard-shell egg which is incubated until hatching of the chick.

In accordance with the present invention, the germinal disc may be a germinal disc of any animal which produces a germinal disc, in particular avians including, but not limited to, chickens, ducks, turkeys, quails, pheasants and ratites.

In one embodiment, the invention is directed to devices useful for the delivery of an object or a substance such as an isolated cell nucleus, a spermatozoon or a fluid containing biomolecules such as nucleic acid by microinjection into an avian embryo or avian embryonic cell including an avian germinal disc. The present invention is also directed to providing methods of microinjecting an isolated cell nucleus, a spermatozoon or a fluid having a nucleic acid therein, into an avian embryo or embryonic cell. In one useful embodiment, the invention provides devices and methods useful for delivering a nucleic acid to an avian embryo or avian embryonic cell. For example, the invention provides for devices and methods useful for delivering a nucleic acid to an avian germinal disc. In one useful embodiment, the invention provides for the delivery of one or more chromosomes to a germ cell or an embryo, for example, a germinal disc. The invention also contemplates the implanting of a microinjected ovum into an avian such as a chicken wherein a hard-shell egg is formed and thereafter develops and hatches as a chick.

With reference, therefore, to FIG. 1, in one particular embodiment, a microinjection device or assembly of the present invention includes a microscope 1, a microinjection system 100 and an obliquely angled macro monitoring unit 60, wherein the microinjection system 100 is oriented with respect to the microscope 1 so as to be able to microinject an object 5 disposed on the microscope 1, and wherein the macro monitoring unit 60 is oriented to monitor the microinjection of the object 5.

The microscope 1 may be operably connected to an objective 2. The microscope 1 has an optical axis 6 passing through the objective 2, that may be coaxial with an incident light source 3, generally an incident light beam, and a stage 7. The optical microscope 1 of the microinjection device or assembly of the present invention may be any optical microscope wherein the objective 2 can be positioned over the object 5 to be viewed. The microscope objective 2 has a magnification of between about ×5 to about ×50, selected according to the size of the object being viewed. For example, the highest (about ×50) magnification may be used to observe the loading of a micropipette. The lowest (about ×5) magnification, for example, may be used for observing microinjection of an avian ovum or embryo. Optionally, the microscope 1 may further comprise a transmitted light source 4, wherein the light from the transmitted light source 4 is directed through an object 5 disposed on the stage 7 of the microscope 1.

It is contemplated to be within the scope of the present invention for the object 5 to be a germinal disc, i.e., an avian ovum or embryo removed from a female bird after ovulation, for example, before deposition of albumen and shell thereon, or a vessel containing a fluid having an isolated nucleic acid or cell nucleus that is to be injected into an avian reproductive cell or germinal disc.

Figure 6:
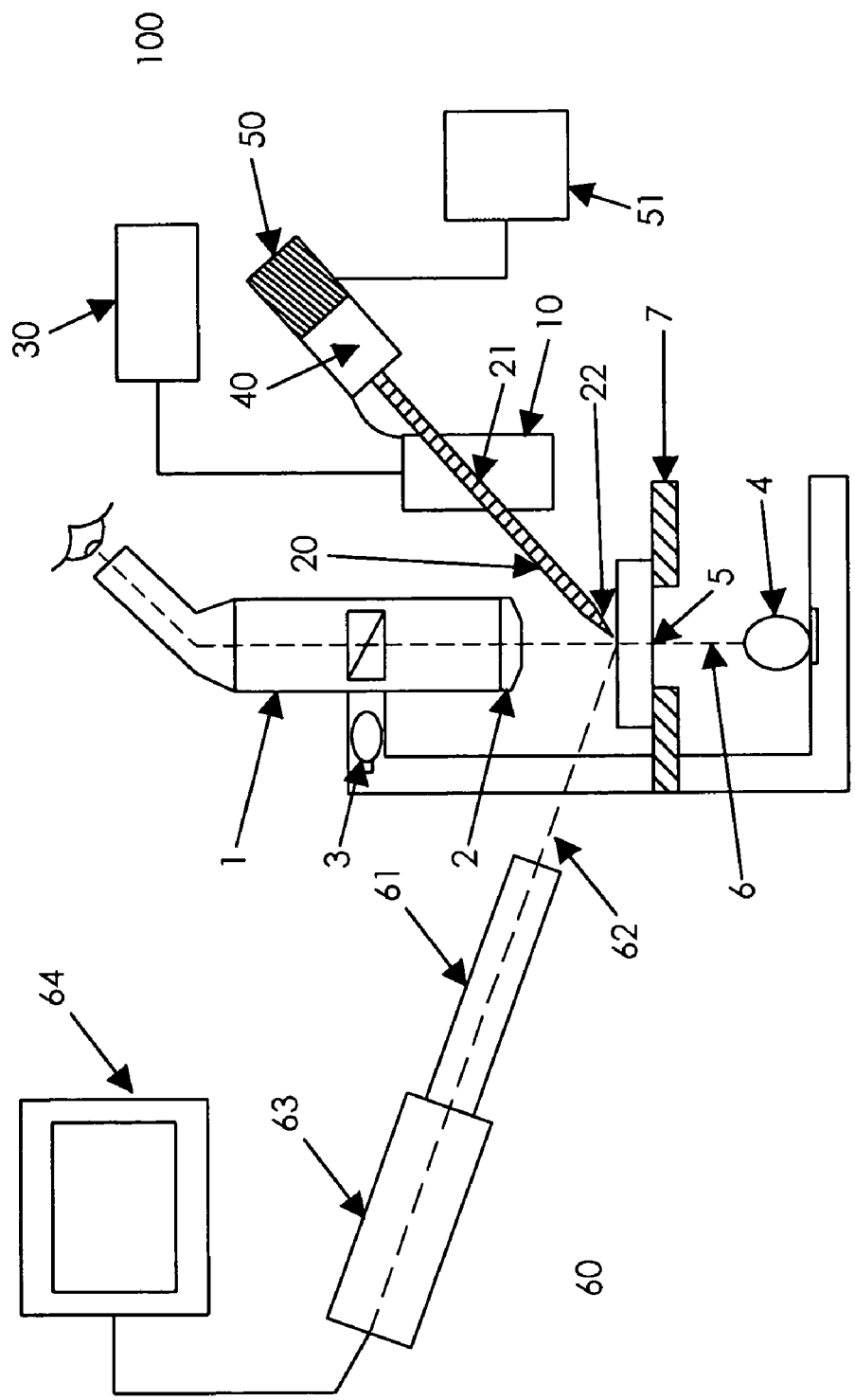
FIG. 6 illustrates one particular microinjection device or assembly of the present invention which may be used for microinjecting a germinal disc.

The microinjection system of FIG. 6 comprises a micromanipulator 10 operably connected to a micropipette 20 wherein the micropipette 20 has a lumen 21 therein and a distal tip 22, and optionally, is operably connected to a programmable control unit 30. Preferably, the micromanipulator 10 can allow the micropipette 20 to be oriented to any position relative to the object 5 disposed on the stage 7 of the microscope 1. Any micromanipulator 10 known to one of skill in the art may be incorporated into a device of the present invention. The microinjection device may further comprise a pressure regulating system 40 such as a pump, for example, an air pump, a liquid pump, or a syringe pump that will allow the operator of the microinjection system 100 of the present invention to apply a positive or negative hydraulic pressure to the lumen 21 of the micropipette 20 so that a fluid may be drawn into, or ejected from, the lumen 21.

The programmable control unit 30 may be operably connected to the micromanipulator 10 and may store electronic signals that define a selected position and angle of the micropipette 20 relative to a predetermined point, such as a predetermined point situated on or near an object 5 disposed on the stage 7 of the microscope 1. The micropipette 20 may then be moved from the predetermined point, and returned to the same, by operating the programmable control unit 30.

A microinjection system 100 of the present invention may also include a piezo-electric oscillator 50 operably connected to the micropipette 20 which may include a control unit 51. An example of a suitable oscillator unit that may be used in the microinjection device or assembly of the present invention is the PIEZODRILL™ Inertial Impact Drill (Burleigh Instruments, Inc.). Operation of the piezo-electric oscillator 50 will impart vibrations of preselected frequency, amplitude and bandwidth to the distal tip 22 of the micropipette 20 directed longitudinally to the lumen 21 of the micropipette 20, or in a direction normal to the lumen 21. The speed of the drilling is controlled by the frequency of oscillations imparted to the distal tip 5 of the micropipette 20. Examples of frequencies contemplated by the present invention are those that range from about 1 Hz to about 100 Hz, for example, between about 1 Hz and about 25 Hz. Bandwidth of the oscillations can regulate the sharpness of the vibrational pulse imparted to the micropipette 20.

The microinjection assemblies of the invention can include an obliquely angled macro monitoring unit 60 comprising a lens 61 having an optical axis 62 directed to the object 5 disposed on the stage 7 of the microscope 1 wherein the optical axis is at an oblique angle to the surface of the object 5. The lens 61 may be operably connected to an electronic camera 63, and to a monitor 64 that displays the image generated by the electronic camera 63. The lens 61 may be focused by adjusting the internal lens configuration thereof, or by moving the lens 61 in a direction along the optical axis 62, to or from the object 5.

Any suitable needle or micropipette 20 may be used in the microinjection assemblies of the present invention. In one embodiment, the internal diameter of the micropipette 20 may be selected as a function of the size of an object, such as a cell nucleus, to be transferred to an avian embryonic cell. For example, the preferred internal diameter of the micropipette may be between about 10 µm and about 15 µm when a nucleus to be transferred to an enucleated avian ovum has been isolated from a blastodermal cell. In one embodiment, the internal diameter is between about 4 µm and about 8 µm, when a nucleus has been obtained from a fibroblast, or is a spermatozoon.

The microinjection devices or assemblies of the present invention are useful for delivering a fluid containing an isolated cell nucleus, a spermatozoon or an isolated nucleic acid component such as, but not limited to, a plasmid or a viral vector, to the cytoplasm or cytoplast of an avian embryonic cell, an avian ovum (oocyte) or an avian embryo. First, an avian ovum, for example, having a pre-stage X germinal disc, is surgically removed from an ovulating hen between about 30 minutes and about 2 hours of the previous laying of a hard-shell egg. This surgically removed avian ovum can then be placed in a specimen container, such as a glass dish, and placed on the stage 7 of the optical microscope 1.

The lumen 21 of the micropipette 20 is loaded with a fluid that is to be injected into the object (e.g., germinal disc, avian embryonic cell or cytoplast). Using the transmitted light source 4 of the microscope to illuminate the micropipette 20, the distal tip 22 of the micropipette 20 can be positioned to remove a nucleus from a donor cell, to gather spermatozoa or to be loaded with a fluid containing an isolated nucleic acid, for example, plasmid or viral DNA or an artificial chromosome. The transmitted light source 4 allows the device operator to monitor the extent of the micropipette charging (i.e., loading of fluid into the micropipette) or to manipulate cells to remove the nucleus therefrom.

In one embodiment, the micropipette 20 is charged with an inert liquid, such as FLOURINERT™ that will transmit piezo-electric induced oscillations from the piezo-electric oscillator 50 to the distal tip 22 of the micropipette 20. All fluids and objects, if applicable, may be drawn into the micropipette by a pump 40 operably connected to the micropipette 20, wherein the pump 40 is capable of positively or negatively regulating the hydraulic pressure in the lumen 21 of the micropipette 20 to ingress or eject the fluid.

Figure 5:
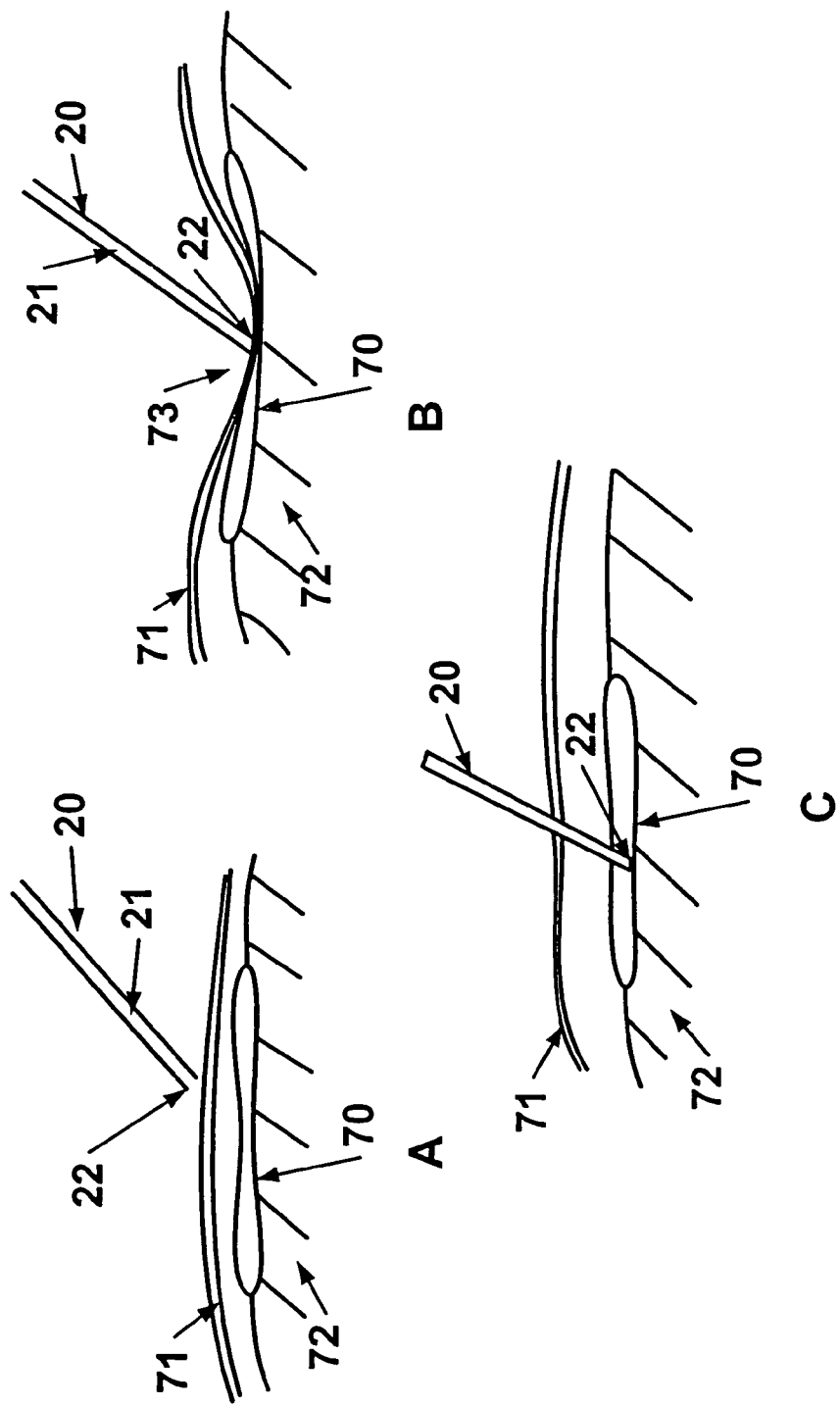
FIGS. 5A, 5B and 5C illustrate an embodiment for insertion of an injection needle of the invention into a germinal disc.

Referring to FIGS. 5A to 5C, in one embodiment, once the micropipette 20 is loaded, the surgically excised egg is placed on the stage 7 of the microscope 1 and illuminated with an incident beam of light. In one embodiment of the microinjection device of the present invention, the incident beam of light is coaxial with the optical axis of the microscope objective. In another embodiment of the device of the present invention, the incident beam of light is angled from the optical axis 6 of the objective 2. Placement of the germinal disc 70 to a predetermined position relative to the microscope 1, and thereby in the optical axis 62 of the macro monitoring unit 60, is facilitated by first positioning the germinal disc 70 in the incident light beam of the microscope 1.

Referring now to FIG. 5A, when the germinal disc 70 of the avian egg is positioned in, and illuminated by, the incident light beam, the micropipette 20 is moved to a preprogrammed selected position whereby the distal tip 22 of the micropipette 20 is over the area of the germinal disc 70 and therefore optimally placed for the insertion of the micropipette 20 into the germinal disc 70. The distal tip 22 of the micropipette 20 is then pressed onto the vitelline membrane 71 of the avian egg, to a depth of about 20 µm below the general plane of the membrane, as shown in FIG. 5B. The vitelline membrane 71 resists penetration by the micropipette 20 and therefore the distal tip 22 indents the vitelline membrane 71 without piercing the membrane 71.

The depth of the indentation 73 formed by the pressure of the distal tip 22 of the micropipette 20 on the vitelline membrane 71 can be determined by at least two methods. The needle or micropipette may be pre-marked about 20 µm from the distal tip 22. When the mark is about level with the general plane of the membrane, the distal tip 22 will enter the germinal disc 70 once the vitelline membrane 71 is penetrated. The distance for the micropipette 20 to be depressed may also be controlled by measuring the micropipette 20 movement, for example, against a precalibrated scale. In one embodiment, the needle is simply positioned so as to touch the membrane.

The movement of the micropipette 20 relative to an avian germinal disc 70 is monitored by the obliquely angled macro monitoring unit 60, comprising a focusable lens 61 capable of delivering a focused magnified image of the avian germinal disc 70 to an electronic camera 63 for display by a monitor 64. The oblique angle of the lens 61 shows the depth of movement of the micropipette 20 relative to the vitelline membrane 71 and the degree of indentation thereof, more distinctly than if a vertical microscope objective 2 is used to monitor the microinjection.

Pulses of piezo-electric induced oscillations are applied to the micropipette 20 once it is in contact with the indented vitelline membrane 71. The vibrating distal tip 22 of the micropipette 20 drills through the vitelline membrane 71. Successful penetration, and therefore placement of the distal tip 22 at a desired position within the avian germinal disc 70, is signaled by the vitelline membrane 71 moving suddenly to its non-indented conformation, as shown in FIG. 5C. The fluid contents of the micropipette 20 can then be injected into the germinal disc 70 by positive hydraulic pressure exerted on the lumen 21 and the contents therein, by the pressure-regulating system 40.

The present invention also provides methods for producing a transgenic bird, such as, but not limited to, a chicken, by introducing a transgene to an avian germinal disc wherein the transgene is included in a nucleic acid component such as a viral or a non-viral vector or an artificial chromosome. The invention also contemplates facilitation of sperm-mediated gene transfer, integration and nuclear transfer via two-photon visualization and optionally, laser-mediated ablation, ovum transfer and the like. Transgenic avians produced by the instant invention may have the ability to lay eggs that contain one or more desired heterologous protein(s) such as pharmaceutical proteins, for example, an immunoglobulin light or heavy chain, an antibody, or variant thereof.

The invention contemplates introduction of transgenes into the ovum of a bird, according to the present invention, by nuclear transfer via two-photon visualization and ablation, wherein the nuclear donor contains a desired heterologous DNA sequence in its genome. One of ordinary skill in the art will be able to readily adapt conventional methods to insert the desired transgene into the genome of the nuclear donor prior to injection of the nuclear donor into a recipient cytoplast. For example, a vector that contains one or more transgene(s), encoding at least one polypeptide chain of an antibody, may be delivered into the nuclear donor cell through the use of a delivery vehicle. The transgene is then transferred along with the nuclear donor into the recipient ovum. Following zygote reconstruction by the methods of the present invention, the ovum is transferred into the reproductive tract of a recipient hen. In a preferred embodiment of the present invention, the ovum may be transferred into the infundibulum of the recipient hen. After reconstruction, the embryo containing the transgene develops inside the recipient hen and travels through the oviduct of the hen where it is encapsulated by natural egg white proteins and a natural egg shell. The egg is laid and can be incubated and hatched to produce a transgenic chick. The resulting transgenic chick will carry one or more desired transgene(s) in its germ line. Following maturation, the transgenic avian may lay eggs that contain one or more desired heterologous protein(s) that can be easily harvested.

Methods for transfection of somatic cell nuclei are well known in the art and include, by way of example, the use of retroviral vectors, retrotransposons, adenoviruses, adeno-associated viruses, naked DNA, lipid-mediated transfection, electroporation and direct injection into the nucleus. Such techniques, particularly as applied to avians, are disclosed by Bosselman (U.S. Pat. No. 5,162,215), Etches (PCT Publication No. WO 99/10505), Hodgson (U.S. Pat. No. 6,027,722), Hughes (U.S. Pat. No. 4,997,763), Ivarie (PCT Publication No. WO 99/19472), MacArthur (PCT Publication No. WO 97/47739), Perry (U.S. Pat. No. 5,011,780), Petitte (U.S. Pat. Nos. 5,340,740 and 5,656,749), and Simkiss (PCT Publication No. WO 90/11355), the disclosures of which are incorporated by reference herein in their entireties. Other patents, the disclosures of which are included in the present application, include U.S. Pat. No. 6,376,743, issued Apr. 23, 2002; U.S. Pat. No. 6,331,659, issued Dec. 18, 2001; and U.S. Pat. No. 6,143,564, issued Nov. 7, 2000.

Another aspect of the present invention contemplates the production of a cloned bird using nuclear transfer methods employing two-photon visualization. The steps in nuclear transfer include, but are not limited to, the preparation of a cytoplast, donor cell nucleus (nuclear donor) isolation and transfer to the cytoplast to produce a reconstructed embryo, optional culturing of the reconstructed embryo, and embryo transfer to a synchronized host animal.

In this method, a fertilized or unfertilized egg may be removed from a bird and manipulated in vitro, wherein the genetic material of the egg is visualized and removed and the ablated nucleus replaced with a donor nucleus. Optionally, the donor nucleus may be genetically modified with, for example, a transgene encoding an exogenous polypeptide. Two-photon laser scanning microscopy (TPLSM) can be used to visualize the nuclear structures. Following visualization, the nucleus in the recipient cell, such as a fertilized or unfertilized egg, is removed or ablated, optionally using TPLSM.

TPLSM produces non-invasive, three-dimensional, real-time images of the optically dense avian egg. Visualization of the metaphase plate or pronucleus in avian eggs during nuclear transfer has been prevented by the yolk. Two-photon imaging with femtosecond lasers operating in the near infrared, however, allows visualization of nuclear structures without damaging cellular constituents. Prior to visualization, specimens may be incubated or injected with DNA-specific dyes such as DAPI (4',6'-diamidino-2-phenylindole hydrochloride) or Hoescht 33342 (bis-benzimide), the albumen capsule is removed and the ovum placed in a dish with the germinal disc facing the top. Remnants of the albumen capsule are removed from the top of the germinal disc.

An aqueous solution, for example phosphate-buffered saline (PBS), may be added to prevent drying of the ovum. A cloning cylinder is placed around the germinal disc and DAPI in PBS is added to the cylinder. Alternatively, a DAPI-PBS solution may be injected into the germinal disc with a glass pipette, whereupon the dye enters the nuclear structures. For dye injection, removal of the albumen capsule is not necessary, whereas injection of nuclei into the disc is facilitated in the absence of the capsule.

Images of the inside of the early avian embryo can be generated through the use of TPLSM. Visualization may be performed after about 10 to 15 minutes of incubation or about 10 minutes after dye injection. During visualization, the germinal disc is placed under the microscope objective and the pronuclear structures are searched within the central area of the disc using relatively low laser powers of about 3-6 milliwatts. Once the structures are found they may be ablated by using higher laser power or be mechanically removed, guided by TPLSM.

Nuclear transfer also requires the destruction or enucleation of the pronucleus before a nuclear donor can be introduced into the oocyte cytoplast. Two-photon laser-mediated ablation of nuclear structures provides an alternative to micro surgery to visualize the pronucleus lying about 25 μm beneath the ovum's vitelline membrane within the germinal disc. Higher laser powers than those used for imaging are used for enucleation, with minimal collateral damage to the cell. The wavelength for ablation generally ranges from about 700 nm to about 1000 nm, at about 30 to about 70 milliwatts. TPLSM and two-photon laser-mediated ablation are more efficient than alternative methods because they are less operator dependent and less invasive, which results in improved viability of the recipient cell.

It is contemplated that a cultured somatic cell nucleus (nuclear donor) may then be injected into the enucleated recipient cytoplast by the microinjection device or assembly of the present invention. The donor nucleus is introduced into the germinal disc through guided injection using episcopic illumination (i.e., light coming through the objective onto the sample). The reconstructed zygote may then be surgically transferred to the oviduct of a recipient hen to produce a hard-shell egg. Alternatively, the reconstructed embryo may be cultured for 24 hours and screened for development prior to surgical transfer.

The egg can be harvested after laying and before hatching of a chick, or further incubated to generate a cloned chick, optionally genetically modified. The cloned chick may carry a transgene in all or most of its cells. After maturation, the transgenic avian may lay eggs that contain one or more desired heterologous protein(s). The cloned chick may also be a knock-in chick expressing an alternative phenotype or capable of laying eggs having a heterologous protein therein. The reconstructed egg may also be cultured to term using the ex ovo method described by Perry, (1988) Nature 331: 70-72, which is incorporated in its entirety herein by reference.

The replacement of the recipient cell's nucleus with the donor cell's nucleus results in a reconstructed zygote. Preferably, the cytoplasmic membrane of the cell used as nuclear donor is disrupted to expose its nucleus to the ooplasm of the recipient cytoplast. The nuclear donor may be injected into the germinal disc, where it undergoes reprogramming and becomes the nucleus of the reconstructed one-cell embryo.

Another aspect of the present invention contemplates producing a cloned bird comprising nuclear transfer in combination with ovum transfer. Two-photon visualization and ablation may be used to perform nuclear transfer, as described above. Accordingly, the replacement of the recipient cell's nucleus with the donor cell's nucleus results in a reconstructed zygote. Preferably, pronuclear stage eggs are used as recipient cytoplasts already activated by fertilization. Alternatively, unactivated metaphase II eggs may serve as recipient cytoplast and activation induced after renucleation. The ovum may then be cultured via ovum transfer, wherein the ovum containing the reconstructed zygote is transferred to a recipient hen. The ovum is surgically transferred into the oviduct of the recipient hen shortly after oviposition. This is accomplished according to normal husbandry procedures (oviposition, incubation, and hatching; see Tanaka et al., supra).

Alternatively, the ovum may be cultured to Stage X prior to transfer into a recipient hen. More specifically, reconstructed stage I embryos are cultured for 24-48 hours to Stage X. This allows for developmental screening of the reconstructed embryo prior to surgical transfer. Stage I embryos are enclosed within a thick albumen capsule. In this novel procedure, the albumen capsule is removed, after which the nuclear donor is injected into the germinal disc using the microinjection device and the methods of use thereof, of the present invention. Subsequently, the capsule and germinal disc are recombined by placing the thick capsule in contact with the germinal disc on top of the yolk. Embryos develop to Stage X at similar rates as those cultured with their capsules intact. At Stage X of development, the embryo is transferred to the oviduct of a recipient hen.

Once transferred, the embryo develops inside the recipient hen and travels through the oviduct of the hen where it is encapsulated by natural egg white proteins and a natural egg shell. The egg that contains endogenous yolk and an embryo from another hen, is laid and can then be incubated and hatched like a normal chick. The resulting chick may carry a transgene in all or most of its cells. Preferably, the transgene is at least in the oviduct cells of the recipient chick. Following maturation, the cloned avian may express a desired phenotype or may be able to lay eggs that contain one or more desired heterologous protein(s).

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the claims. In addition, it should be understood that aspects of the various embodiments may be interchanged both in whole or in part. The present invention is further illustrated by the following examples, which are provided by way of illustration and should not be construed as limiting. The contents of all references, published patents and patents cited throughout the present application are also hereby incorporated by reference in their entireties.

Reference will now be made in detail to the certain embodiments of the invention. Each example is provided by way of explanation of the invention, not limitation of the invention. In fact, it will be apparent to those skilled in the art that various modifications, combinations, additions, deletions and variations can be made in the present invention without departing from the scope or spirit of the invention. For instance, features illustrated or described as part of one embodiment can be used in another embodiment to yield yet another embodiment. It is intended that the present invention covers such modifications, combinations, additions, deletions and variations as fall within the scope of the appended claims and their equivalents.

Throughout this application various publications are referenced. The disclosures of these publications in their entireties are hereby incorporated by reference in this application to more fully describe the state of the art to which this invention pertains.

EXAMPLE 1

Production of Transgenic Hens by Microinjection of an Ovomucoid Promoter-Bacterial Artificial Chromosome Expression Vector Transgene BAC clones OMC24-IRES-LC and OCM24-IRES-HC were used to produce transgenic chickens by microinjection. A detailed description of these BACs is disclosed in U.S. patent application Ser. No. 11/047,184, filed Jan. 31, 2005 now allowed, the disclosure of which is incorporated in its entirety herein by reference. Briefly, each BAC includes a 70 kb chicken ovomucoid gene region with a coding sequence for either a heavy chain (HC) or light chain (LC) of a particular human IgG1 antibody. The HC and LC sequences are under the translational control of an internal ribosome entry site (IRES) which is inserted in the 5' UTR of the ovomucoid gene region.

The BACs were linearized by enzymatic restriction digest. The digested DNA was phenol/CHCl$_3$ extracted, ethanol precipitated, suspended in 0.25 M KCl and diluted to a working concentration of approximately 60 µg/ml (30 µg/ml OMC24-IRES-LC and 30 µg/ml OMC24-IRES-HC) with SV40 T antigen nuclear localization signal peptide (NLS) added yielding a peptide:DNA molar ratio of 100:1 (Collas and Alestrom, 1996, Mol. Reprod. Develop. 45: 431-438, the disclosure of which is incorporated by reference in its entirety). The DNA samples were allowed to associate with the SV40 T antigen NLS peptide by incubation at room temperature for 15 minutes.

Introduction of the DNA-NLS complex into an avian egg was accomplished by microinjection employing the device shown in FIG. 1. A stage I White Leghorn chicken embryo was immersed in Ringer's buffer and the germinal disc was visualized using a 6 mm submersible borescope mounted on a heavy-duty micromanipulator (Siskiyou Design Instruments Inc, catalogue # MX1640). An injection needle, mounted on a second micromanipulator, comprising a drawn out glass capillary tube having a beveled tip approximately 20 µm in length was positioned by micromanipulation such that the tip of the needle formed a dimple or invagination of about 15 to 20 µm in depth in the vitelline and oolemma membranes of the germinal disc (FIG. 4B). A 635 nm/25 mW laser (Coherent Radius 635-25) was used to deliver laser light to the needle by a fiber optic line providing illumination of the needle and a color contrast between the tip of the needle and the surface of the yolk thereby facilitating an enhanced visualization of the injection needle tip. The needle was also operably attached to a piezo unit comprising a signal generator (BK Precision Model # 4011A) capable of operating at a frequency of 5 KHz; an amplifier (Physik Instrumente GmbH, amplifier: PI-Polytec E-505 PZT-Power Amplifier, average power 30 W, output voltage −20 to +120 V and optimized for 100V PiezoDrive); and a Piezo actuator (Physik Instrumente GmbH, catalog # P-840. 10).

The piezo unit was set to 3100 Hz with a travel distance of about 5 µm for latitudinal vibration and was activated for approximately 0.5 sec. The injection needle penetrated the vitelline membrane and the oolemma of the germinal disc to a depth of about 15 to 20 µM, the bevel of the needle being mostly submerged under the vitelline membrane with only the uppermost portion of the bevel being visible above the membranes (See, FIG. 4B). The DNA-NLS was then injected into the germinal disc by employing a pico-injector system (Harvard Apparatus PLI-100) which is operably linked to the injection needle. Approximately 100 nanoliters of DNA were injected into a germinal disc.

Injected embryos were surgically transferred to recipient hens via ovum transfer according to the method of Christmann et al. (see, for example, U.S. patent application Ser. No. 10/679,034, filed Oct. 2, 2003, the disclosure of which is incorporated herein in its entirety by reference) and hard shell eggs were incubated and hatched. See, Olsen and Neher, 1948, J. Exp. Zoo. 109: 355-366, the disclosure of which is incorporated in its entirety herein by reference.

Genomic DNA samples from one-week old chicks were analyzed for the presence of OMC24-IRES-LC and OMC24-IRES-HC by PCR using methods well known in the field of avian transgenics. Briefly, three hundred nanograms of genomic DNA and 1.25 units of Taq DNA polymerase (Promega) were added to a 50 µl reaction mixture of 1×Promega PCR Buffer with 1.5 mM MgCl$_2$, 200 µM of each dNTP, 5 µM primers. The reaction mixtures were heated for 4 minutes at 94° C., and then amplified for 34 cycles each consisting of: 94° C. for 1 min, 60° C. for 1 min and 72° C. for 1 min. A final cycle of 4 minutes at 72° C. was performed. PCR products were detected by visualization on a 0.8% agarose gel stained with ethidium bromide.

EXAMPLE 2

Production of Antibody by Transgenic Hens

Transgenic chicks produced as described in Example 1 were grown to maturity. Eggs were collected from the hens and egg white material was assayed for the IgG1 using sandwich ELISA.

The eggs were cracked and opened and the whole yolk portion was discarded. Both the thick and thin egg white portions were kept. 1 ml of egg white was measured and added to a plastic Stomacher 80 bag. A volume of egg white buffer (5% 1M Tris-HCl pH 9 and 2.4% NaCl) equal to two times the volume of egg white was added to the egg white. The egg white-buffer mixture was paddle homogenized in the Stomacher 80 at normal speed for one minute. The sample was allowed to stand overnight and homogenation was repeated. A 1 ml sample of the mixture was used for testing.

A Costar flat 96-well plate was coated with 100 ul of C Goat-anti-Human kappa at a concentration of 5 µg/ml in PBS. The plate was incubated at 37° C. for two hours and then washed. 200 µl of 5% PBA was added to the wells followed by an incubation at 37° C. for about 60-90 minutes followed by a wash. 100 ul of egg white samples (diluted in 1% PBA:LBP) was added to each well and the plate was incubated at 37° C. for about 60-90 min followed by a wash. 100 ul of a 1:2000 dilution of F'2 Goat anti-Human IgG Fc-AP in 1% PBA was added to the wells and the plate was incubated at 37° C. for 60-90 min followed by a wash.

The transgenic antibody was detected by placing 75 ul of 1 mg/ml PNPP (p-nitrophenyl phosphate) in 5x developing buffer in each well and incubating for about 10-30 mins at room temperature. The detection reaction was stopped using 75 ul of 1N NaOH. The OD405-650 nm was then determined for each sample well. Each OD405-650 nm value was compared to a standard curve to determine the amount of recombinant antibody present in each sample. Approximately 0.3% of hens analyzed expressed antibody in their eggs. Two hens which expressed antibody are Hen 1251 which was found to produce an average of 19 ng of IgG per ml of egg white and Hen 4992 which was found to produce an average of 150 ng of IgG per ml of egg white.

EXAMPLE 3

Production of Transchromosomic Chickens Using Satellite DNA-Based Artificial Chromosomes Satellite DNA-based artificial chromosomes (ACEs, as described in Lindenbaum et al Nucleic Acids Res (2004) vol 32 no. 21 e172) were isolated by a dual laser high-speed flow cytometer as described previously (de Jong, G, et al. Cytometry 35: 129-133, 1999).

The flow-sorted chromosomes were pelleted by centrifugation of a 750 µl sample containing approximately $10^6$ chromosomes at 2500xg for 30 min at 4° C. The supernatant, except the bottom 30 microliters (µl) containing the chromosomes, was removed resulting in a concentration of about 7000 to 11,500 chromosomes per µl of injection buffer (Monteith, et al. Methods Mol Biol 240: 227-242, 2004). Depending on the number of chromosomes to be injected, 25-100 nanoliters (nl) of injection buffer was injected per embryo.

Embryos for this study were collected from 24-36 week-old hens from commercial White Leghorn variety of *G. gallus*. Embryo donor hens were inseminated weekly using pooled semen from roosters of the same breed to produce eggs for injection.

On the day of egg collection, fertile hens were euthanized 2 h post oviposition by cervical dislocation. Typically, oviposition is followed by ovulation of the next egg after about 24 minutes (Morris, Poultry Science 52: 423-445, 1973). The recently ovulated and fertilized eggs were collected from the upper magnum region of the oviduct under sterile conditions and placed in a glass well and covered with Ringers' Medium (Tanaka, et al. J Reprod Fertil 100: 447-449, 1994) and maintained at 41° C. until microinjection.

Injection of artificial chromosomes into a stage I embryo was achieved using the microinjection apparatus shown in FIG. 1 essentially as disclosed in Example 1. Chromosomes were injected into the stage I embryos at a single site. Each embryo was injected with approximately: 175, 250, 350, 450, 550, 800 or >1000 chromosomes. The chromosomes were injected in a suspension of 25-100 nanoliters (nl) of injection buffer.

Following microinjection, the embryos were transferred to the oviduct of recipient hens using an optimized ovum transfer (OT) procedure (Olsen, M and Neher, B. J Exp Zool 109: 355-66, 1948), with the exception that the hens were anesthetized by Isofluorane gas. Typically, about 26 h after OT, the recipient hens lay a hard shell egg containing the manipulated ovum. Eggs were incubated for 21 days in a regular incubator until hatching of the birds.

The chromosomes were injected into the embryos over a 9 day period. The chromosomes were divided into three batches for delivery to the embryos each batch being injected over a three day period. Chromosomes were introduced into the embryos by a single injection. Following injection, each egg was transferred to a recipient hen. A total of 301 transfers were performed, resulting in 226 (75%) hard shells and 87 hatched chicks (38%, see Table 2).

TABLE 2

Hatching of embryos microinjected with satellite DNA-based artificial chromosomes.

| | Ovum transfers | Hard shells produced | hatched birds |
|---|---|---|---|
| 1st batch | 71 | 53 | 15 |
| 2nd batch | 113 | 80 | 33 |
| 3rd batch | 117 | 93 | 39 |
| Totals | 301 | 226 (75%) | 87 (38%) |

Previous experiments have determined that hatching is not significantly affected when embryos were injected with up to 100 nl of injection buffer. Satellite DNA-based artificial chromosomes were injected in suspensions of between 25-100 nl of injection buffer.

As discussed, the embryos were injected with one of seven different numbers of artificial chromosomes. All transchromosomic birds in the present study were obtained from embryos injected with 550 chromosomes or less (see Table 3).

Six transchromosomic founders were produced based on two separate PCR analysis (6.8%, see Table 3) using primers which anneal to the puromycin resistance gene (about 75 copies of the $pur^R$ gene are present on the chromosome). All positive birds appear normal.

TABLE 3

Effect of the number of Chromosomes injected per embryo on hatching and number of transchromosomic birds produced.

| # chromosomes injected per embryo | # of hard shells | # chicks hatched | # of positive birds (bird tag #) |
|---|---|---|---|
| 175 | 31 | 11 (35%) | 3 (BB7478, BB7483, BB7515) |
| 250 | 51 | 25 (49%) | 1 (BB7499) |
| 350 | 15 | 6 (40%) | 0 |
| 450 | 31 | 11 (35%) | 0 |
| 550 | 39 | 17 (43%) | 2 (BB7477, BB7523) |
| 800 | 26 | 5 (19%) | 0 |
| 1000 | 33 | 10 (30%) | 0 |
| Totals | 226 | 87 (38%) | 6 (6.8%) |

To confirm the PCR results, erythrocytes from all PCR-positive birds as well as fibroblast cells derived from skin biopsies of 5 PCR-positive birds were analyzed by interphase and metaphase FISH using a mouse-specific major satellite DNA probe (Co, et al. Chromosome Res 8: 183-191, 2000). Five of the six chicks (5.3% out of total number of chicks analyzed) tested by FISH were positive in at least one cell type (see Table 4) at 3 weeks of age. FISH analysis of erythrocytes was repeated when the birds reached 8 weeks of age and had tripled their body weight. Similar numbers of artificial chromosome-positive cells found in each bird were observed in this second FISH analysis.

TABLE 4

Summary of FISH analysis of Red Blood Cells (RBCs) and fibroblast cells derived from transchromosomic birds. Fibroblast cells from hen # 7515 were not available for analysis.

| Bird # | Sex of Bird | % of artificial chromosome positive RBCs by FISH | % of artificial chromosome positive fibroblasts by FISH |
|---|---|---|---|
| BB7499 | Female | 77% | 87% |
| BB7483 | Female | 0.8% | 0% |
| BB7477 | Male | 3% | 2.8% |
| BB7478 | Male | 15% | 3% |
| BB7515 | Female | 1.3% | NA |
| BB7523 | Male | 0% | 0% |
| Neg. control | — | 0% | 0% |

To verify the chromosomes were intact, metaphase spreads from fibroblast cells derived from founders were made as described previously (Garside and Hillman (1985) Experientia 41: 1183-1184). FISH analysis of metaphase spreads using the major satellite DNA probe showed the artificial chromosomes appear intact, with no apparent fragmentation or translocation onto the chicken's chromosomes. FISH analysis using a mouse minor satellite probe, which detects the centromeric region of the introduced chromosomes (Wong and Rattner (1988) J. Nucleic Acids Res 16: 11645-11661), demonstrated the centromere of the chromosomes was intact. Furthermore, the percentage of satellite DNA-based artificial chromosomes positive cells from metaphase spreads agreed closely to those observed in interphase FISH.

Analysis of G1 embryos from test birds BB7499 and BB7477 has shown the artificial chromosome to be transmitted through the germline.

EXAMPLE 4

Production of EPO and G-CSF Vectors for the Production of Transchromosomic Chickens Two vectors were constructed for introduction into Satellite DNA-based artificial chromosomes. 1OMC24-IRES1-EPO-ChromattB was constructed by inserting an EPO coding sequence into an OMC24-IRES BAC clone disclosed in U.S. patent application Ser. No. 10/856,218, filed May 28, 2004, now U.S. Pat. No. 7,294,507, the disclosure of which is incorporated in its entirety herein by reference. The EPO coding sequence was inserted in the clone so as to be under the control of the ovomucoid promoter. That is, the EPO coding sequence was inserted in place of the LC portion of OMC-IRES-LC. An attB site and a hygromycin$^R$ coding sequence were also inserted into the vector in such a manner as to facilitate recombination into an attP site in a SATAC artificial chromosome (i.e., ACE). The attP site in the SATAC is located adjacent to an SV40 promoter which provides for expression of the hygromycin$^R$ coding sequence upon integration of the vector into the attP site allowing for selection of cells containing a recombinant artificial chromosome (see, for example, U.S. Pat. No. 6,743,967, issued Jun. 1, 2004; U.S. Pat. No. 6,025,155, issued Feb. 15, 2000 and Lindenbaum et al Nucleic Acids Res (2004) vol 32 no. 21 e172 (see FIG. 25), the disclosure of each of these two patents and the publication are incorporated in their entirety herein by reference).

A coding sequence for G-CSF, which was codon optimized for expression in chicken tubular gland cells, was inserted in the 1OMC24-IRES1-EPO-ChromattB construct in place of the EPO coding sequence to produce 1OMC24-IRES-GCSF-ChrommattB.

EXAMPLE 5

Microinjection of Artificial Chromosomes Encoding Erythropoietin and G-CSF

Cells containing the recombinant artificial chromosome are produced and identified as described in Lindenbaum et al Nucleic Acids Res (2004) vol 32 no. 21 e172. Briefly, 2.5 µg of 1OMC24-IRES1-EPO ChromattB and 2.5 µg of an expression vector which contains a lambda integrase gene (int) having a codon mutation at position 174 to substitute a lysine for a glutamine (pCXLamROK, see Lindenbaum et al Nucleic Acids Res (2004) vol 32 no. 21 e172) are transfected by standard lipofection methodologies into LMTK-cells which contain the platform SATAC (ACE) (A of FIG. 25). Hygromycin resistant cell clones are identified by standard antibiotic selection methodologies.

Recombinant chromosomes are prepared from the cells and isolated by flow cytometry. The substantially purified artificial chromosomes are introduced into chickens by microinjection into stage I embryos as disclosed in Example 3. Resulting chimeric germline transchromosomal avians can be identified by any useful method such as Southern blot analysis.

EXAMPLE 6

Microinjection of Artificial Chromosomes Encoding a Monoclonal Antibody in Turkey Artificial chromosomes comprising a Drosophila chromosome centromere (DAC) are prepared essentially using methods described in U.S. Pat. No. 6,025,155, issued Feb. 15, 2000, the disclosure of which is incorporated in its entirety herein by reference.

An attB site and a hygromycin$^R$ coding sequence are inserted into the OMC24-IRES-LC and OMC24-IRES-HC vectors disclosed in U.S. patent application Ser. No. 10/856, 218, filed May 28, 2004, now U.S. Pat. No. 7,294,507, which are then each cloned into a DAC essentially as described in Example 5. The recombinant DACs are prepared and then isolated by a dual laser high-speed flow cytometer.

The flow-sorted chromosomes are pelleted by centrifugation and are diluted to a concentration of about 7000-12,000 chromosomes per µl of injection buffer. Approximately 50 nanoliters (nl) of injection buffer is injected per turkey embryo.

Embryos for this study are collected from actively laying commercial turkeys. Embryo donor turkeys are inseminated weekly using pooled semen from male turkeys of the same breed to produce eggs for injection.

On the day of egg collection, fertile hens are euthanized 2 h post oviposition by cervical dislocation. The recently ovulated and fertilized eggs are collected from the upper magnum region of the oviduct under sterile conditions and placed in a glass well and covered with Ringers' Medium and maintained at about 40° C. until microinjection.

Cytoplasmic injection of artificial chromosomes containing the OMC24-IRES-LC is achieved essentially as disclosed in Example 3. Approximately 500 chromosomes are injected into the stage I embryos at a single site.

Following microinjection, the embryos are transferred to the oviduct of recipient turkeys essentially as described in Olsen et al, B. J Exp Zool 109: 355-66, 1948. Typically, about one day after OT, the recipient turkeys lay a hard shell egg containing the manipulated ovum. Eggs are incubated in an incubator until hatching of the birds.

G2 transchromosomal turkeys are obtained which contain the artificial chromosome in their genome. The artificial chromosome containing the OMC24-IRES-HC is introduced into embryos obtained from the G2 turkeys in essentially the same manner as described for the OMC24-IRES-LC.

Eggs from G1 transchromosomal turkeys which contain both the OMC-IRES-LC and OMC24-IRES-HC containing chromosomes in their genome are tested for the presence of intact functional monoclonal antibody. A Costar flat 96-well plate is coated with 100 µl of C Goat-anti-Human kappa at a concentration of 5 µg/ml in PBS. The plate is incubated at 37° C. for two hours. 200 µl of 5% PBA is added to the wells followed by an incubation at 37° C. for about 60-90 minutes followed by a wash. 100 µl of egg white samples (diluted in 1% PBA:LBP) is added to each well and the plate is incubated at 37° C. for about 60-90 min followed by a wash. 100 µl of a 1:2000 dilution of F'2 Goat anti-Human IgG Fc-AP in 1% PBA is added to the wells and the plate is incubated at 37° C. for 60-90 min followed by a wash. The antibody is detected by placing 75 µl of 1 mg/ml PNPP (p-nitrophenyl phosphate) in 5× developing buffer in each well and incubating for about 10-30 mins at room temperature. The detection reaction is stopped using 75 ul of 1 N NaOH. The egg white tests positive for significant levels of the antibody.

EXAMPLE 7

Injection of Artificial Chromosomes Encoding Interferon in Quail

Artificial chromosomes comprising a chicken (Barred-Rock) chromosome centromere (CAC) are prepared essentially using methods described in U.S. Pat. No. 6,743,967, issued Jun. 1, 2004, the disclosure of which is incorporated in its entirety herein by reference.

A coding sequence for interferon alpha 2b disclosed in U.S. patent application Ser. No. 10/463,980, filed Jun. 17, 2003, the disclosure of which is incorporated in its entirety herein by reference, is inserted in the 1OMC24-IRES1-EPO-ChromattB construct disclosed herein in Example 4 in place of the EPO coding sequence to produce 1OMC24-IRES-INF-ChrommattB. The 1OMC24-IRES-INF-ChrommattB is cloned into the CACs essentially as described in Example 5. The recombinant CACs are prepared then isolated by a dual laser high-speed flow cytometer.

The flow-sorted chromosomes are pelleted by centrifugation and are diluted to a concentration of about 10,000 chromosomes per µl of injection buffer. Approximately 50 nanoliters (nl) of injection buffer is injected per quail embryo.

Embryos for this study are collected from actively laying quail. Embryo donor quail are inseminated weekly using pooled semen from male quail of the same breed to produce eggs for injection.

On the day of egg collection, fertile quail are euthanized 2 h post oviposition by cervical dislocation. The recently ovulated and fertilized eggs are collected from the upper magnum region of the oviduct under sterile conditions and placed in a glass well and covered with Ringers' Medium and maintained at about 40° C. until microinjection.

Cytoplasmic injection of artificial chromosomes is achieved essentially as disclosed in Example 3. Chromosomes are injected into the stage I embryos at a single site in each embryo.

Following microinjection, the embryos are transferred to the oviduct of recipient quail essentially as described in Olsen et al, B. J Exp Zool 109: 355-66, 1948. Typically, about one day after OT, the recipient quail lay a hard shell egg containing the manipulated ovum. Eggs are incubated in an incubator until hatching of the birds.

Eggs from G2 transchromosomal quail test positive for the presence of intact functional interferon alpha 2b.

EXAMPLE 8

Generation of attP Transgenic Cell Line and Birds Using an NLB Vector

The NLB-attP retroviral vector is injected into stage X chicken embryos laid by pathogen-free hens. A small hole is drilled into the egg shell of a freshly laid egg, the shell membrane is cut away and the embryo visualized by eye. With a drawn needle attached to a syringe, 1 to 10 µl of concentrated retrovirus, approximately $2.5 \times 10^5$ IU, is injected into the subgerminal cavity of the embryo. The egg shell is resealed with a hot glue gun. Suitable methods for the manipulation of avian eggs, including opening and resealing hard shell eggs are described in U.S. Pat. No. 5,897,998, issued May 27, 1999 and U.S. Pat. No. 6,397,777, issued Jun. 4, 2002, the disclosures of which are herein incorporated by reference in their entireties.

Typically, 25% of embryos hatch 21 days later. The chicks are raised to sexual maturity and semen samples are taken. Birds that have a significant level of the transgene in sperm DNA will be identified, typically by a PCR-based assay. Ten to 25% of the hatched roosters will be able to give rise to G1 transgenic offspring, 1 to 20% of which may be transgenic. DNA extracted from the blood of G1 offspring is analyzed by PCR and Southern analysis to confirm the presence of the intact transgene. Several lines of transgenic roosters, each with a unique site of attP integration, are then bred to non-transgenic hens, giving 50% of G2 transgenic offspring. Transgenic G2 hens and roosters from the same line can be bred to produce G3 offspring homozygous for the transgene. Homozygous offspring will be distinguished from hemizygous offspring by quantitative PCR. The same procedure can be used to integrate an attB or attP site into transgenic birds.

EXAMPLE 9

Microinjection of attP Stage I Embryos with OMC24-attB-IRES-CTLA4

Transgenic chickens are produced by injection directly into the germinal disc of stage I embryos of transgenic homozygous attP chickens fertilized with sperm from the same line of homozygous attP roosters. The attP line is produced as described in Example 8. The injections are carried out essentially as described in Example 1.

Stage I embryos are isolated 45 min to 4 h after oviposition of the previous egg. An isolated embryo is placed in a dish with the germinal disc upwards. Ringer's buffer medium is added to prevent drying of the ovum.

Approximately 25 nl of a DNA solution (about 60 ng/µl) of the 77 kb OMC24-attB-IRES-CTLA4, disclosed in U.S. patent application Ser. No. 10/856,218, filed May 28, 2004, now U.S. Pat. No. 7,294,507, with either integrase mRNA or protein are injected into a germinal disc of the isolated stage I embryos as disclosed in Example I. Typically, the concentration of integrase mRNA used is 100 ng/µl or the concentration of integrase protein is 66 ng/µl.

To synthesize the integrase mRNA, a plasmid template encoding the integrase protein is linearized at the 3' end of the transcription unit mRNA is synthesized, capped and a polyadenine tract added using the mMESSAGE mMACHINE T7 Ultra Kit™ (Ambion, Austin, Tex.). The mRNA is purified by extraction with phenol and chloroform and precipitated with isopropanol. The integrase protein is expressed in *E. coli* and purified as described by Thorpe et al, Mol. Microbiol., 38: 232-241 (2000).

Injected embryos are surgically transferred to a recipient hen as described in Olsen & Neher, J. Exp. Zool., 109: 355-66 (1948) and Tanaka et al, J. Reprod. Fertil., 100: 447-449 (1994). The embryo is allowed to proceed through the natural in vivo cycle of albumin deposition and hard-shell formation. The transgenic embryo is then laid as a hard-shell egg which is incubated until hatching of the chick. Injected embryos are surgically transferred to recipient hens via the ovum transfer and hard shell eggs are incubated and hatched.

The chicks produced by this procedure are screened for the presence of the injected transgene using a high throughput PCR-based screening procedure as described in Harvey et al, Nature Biotech., 20: 396-399 (2002). Approximately 20% of the chicks are positive for the transgene. Eggs from each of the mature hens carrying the transgene are positive for CTLA4.

All references cited herein are incorporated by reference herein in their entirety and for all purposes to the same extent as if each individual publication, patent or patent application is specifically and individually indicated to be incorporated by reference in its entirety for all purposes.

The citation of any publication is for its disclosure prior to the filing date and should not be construed as an admission that the present invention is not entitled to antedate such publication by virtue of prior invention.

While this invention has been described with respect to various specific examples and embodiments, it is to be understood that the invention is not limited thereto and that it can be variously practiced with the scope of the following claims.

What is claimed is:

1. A method comprising:
   viewing a germinal disc under magnification at an angle to the germinal disc of less than 90°; and
   injecting a nucleic acid component to the germinal disc through a needle.

2. The method of claim 1 wherein the nucleic acid component is a vector.

3. The method of claim 2 wherein the vector is a non-viral vector.

4. The method of claim 1 wherein the germinal disc is a chicken germinal disc.

5. The method of claim 1 comprising delivering the germinal disc to the oviduct of a recipient avian female.

6. The method of claim 1 comprising inserting the needle into the germinal disc.

7. The method of claim 6 wherein inserting the needle into the germinal disc comprises penetrating a vitelline membrane.

8. The method of claim 1 comprising allowing the germinal disc to develop into a chick.

9. The method of claim 1 wherein the needle includes a bevel.

10. The method of claim 1 wherein an oscillator imparts an oscillation to the needle.

11. The method of claim 1 wherein the oscillation of the needle includes an amplitude of between about 0.001 nm and about 100 µm.

12. The method of claim 1 wherein the angle is between about 30° and about 70°.

13. The method of claim 1 wherein the viewing is through a lens.

14. The method of claim 1 wherein the viewing is through a borescope.

15. A method comprising:
    viewing the surface of a germinal disc under magnification at an angle to the germinal disc of less than 90° and
    injecting a substance to the germinal disc through a needle.

16. A method comprising:
    viewing a germinal disc under magnification at an angle to the germinal disc of between about 1° and about 89°;
    inserting a needle into the germinal disc; and
    injecting a nucleic acid component into the germinal disc through the needle.

17. The method of claim 16 wherein the nucleic acid component is a vector.

18. The method of claim 17 wherein the vector is a non-viral vector.

19. The method of claim 16 wherein the germinal disc is a chicken germinal disc.

20. The method of claim 16 comprising delivering the germinal disc to the oviduct of a recipient avian female.

21. The method of claim 16 comprising inserting the needle into the germinal disc.

22. The method of claim 16 wherein inserting the needle into the germinal disc comprises penetrating a vitelline membrane.

23. The method of claim 16 comprising allowing the germinal disc to develop into a chick.

24. The method of claim 16 wherein the needle includes a bevel.

25. The method of claim 16 wherein an oscillator imparts an oscillation to the needle.

26. The method of claim 16 wherein the oscillation of the needle includes an amplitude of between about 0.001 nm and about 100 µm.

27. The method of claim 16 wherein the angle is between about 30° and about 70°.

28. The method of claim 16 wherein the viewing is through a lens.

29. The method of claim 16 wherein the viewing is through a borescope.

* * * * *